United States Patent [19]

Pang et al.

[11] Patent Number: 5,739,274
[45] Date of Patent: Apr. 14, 1998

[54] ACTIVE COMPONENT OF PARATHYROID HYPERTENSIVE FACTOR

[75] Inventors: Peter K. T. Pang, Sherwood Park; Christina G. Benishin, Androssan; Shan Jie; Richard Z. Lewanczuk, both of Edmonton, all of Canada

[73] Assignee: CV Technologies, Inc., Alberta, Canada

[21] Appl. No.: 387,820

[22] PCT Filed: Jun. 14, 1993

[86] PCT No.: PCT/US93/05626

§ 371 Date: Feb. 24, 1995

§ 102(e) Date: Feb. 24, 1995

[87] PCT Pub. No.: WO93/25577

PCT Pub. Date: Dec. 23, 1993

[51] Int. Cl.$^6$ .................................................. C07K 7/04
[52] U.S. Cl. .................... 530/324; 530/325; 530/326; 530/327; 530/328; 530/329; 530/333; 514/2; 514/7
[58] Field of Search .......................... 514/2, 12, 14, 514/13, 15, 16, 7; 530/324, 325, 326, 327, 328, 329, 333

[56] References Cited

U.S. PATENT DOCUMENTS 5,554,728  9/1996  Basava et al. ........................ 530/327

OTHER PUBLICATIONS

Benishin et al., "Purification of parathyroid hypertensive fctor from plasma of spontaneously hypertensive rats", Proc. Natl. Acad. Sci. USA, vol. 88, pp. 6372–9376, 1991.

Rudinger, Peptide Hormones, (ed. Parsons, J.A.), Baltimore, University Park Press, pp. 1–7, 1976.

Primary Examiner—Cecilia J. Tsang
Assistant Examiner—Anish Gupta
Attorney, Agent, or Firm—Nikaido Marmelstein Murray & Oram LLP

[57] ABSTRACT

An active component of parathyroid hypertensive factor (PHF) which comprises a polypeptide linked to a phospholipid has been identified. The component has activities substantially similar to parathyroid hypertensive factor and therefore is indicated in the control of extracellular calcium uptake, and is related to hypertension and some other diseases in mammals. Method for screening patients for the presence of the circulating factor using antibodies against the component are described. Antagonists of the parathyroid hypertensive factor component have been developed and their use in methods of treating patients with diseases which involve intracellular calcium elevation are also described.

23 Claims, 15 Drawing Sheets

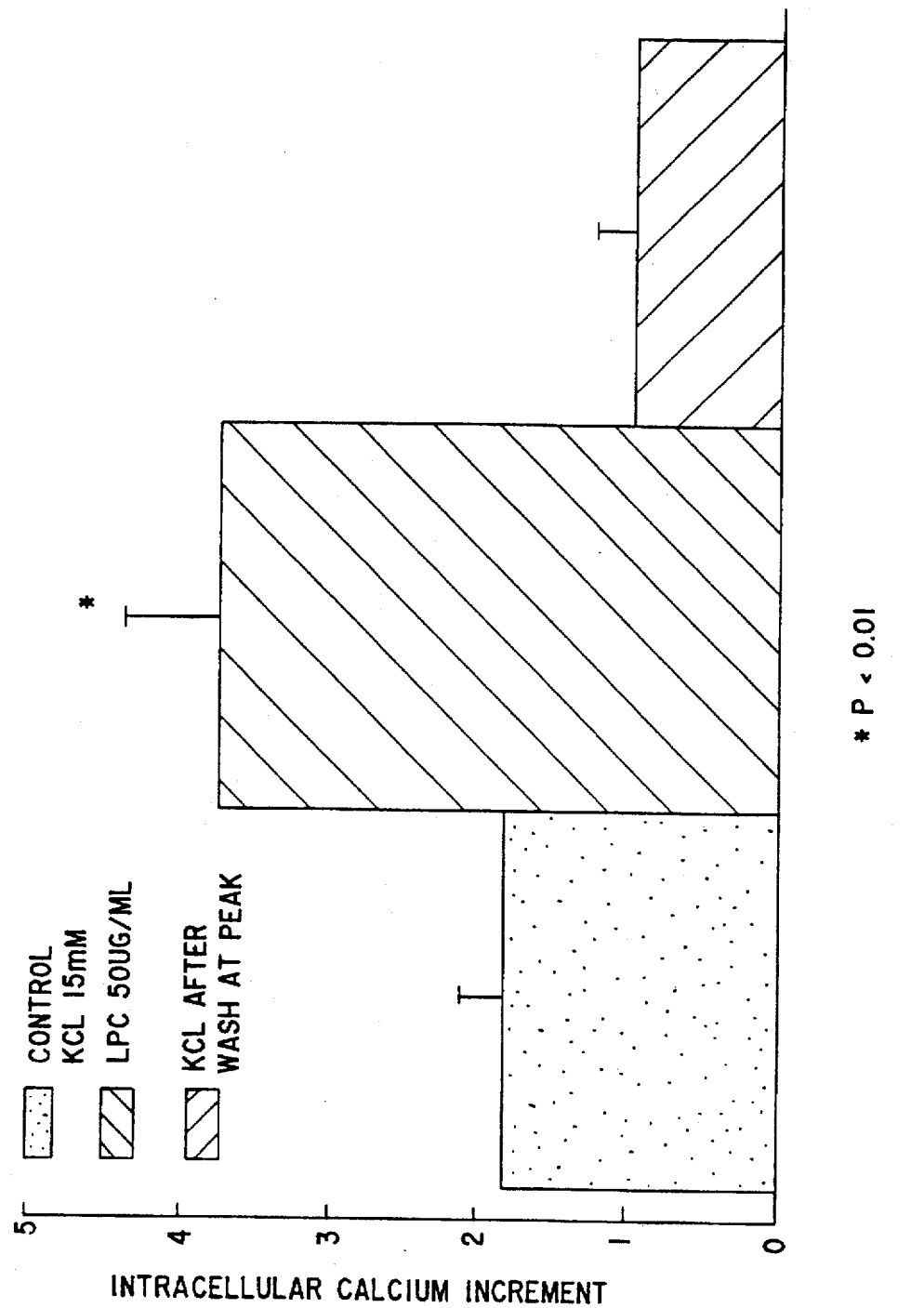

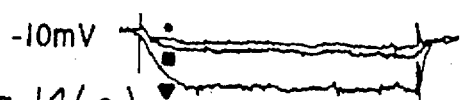
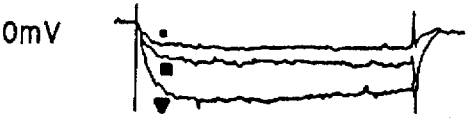
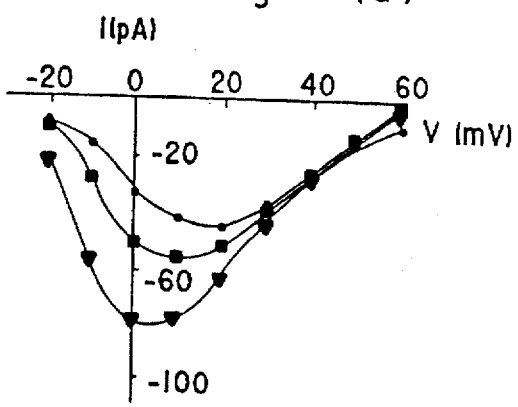
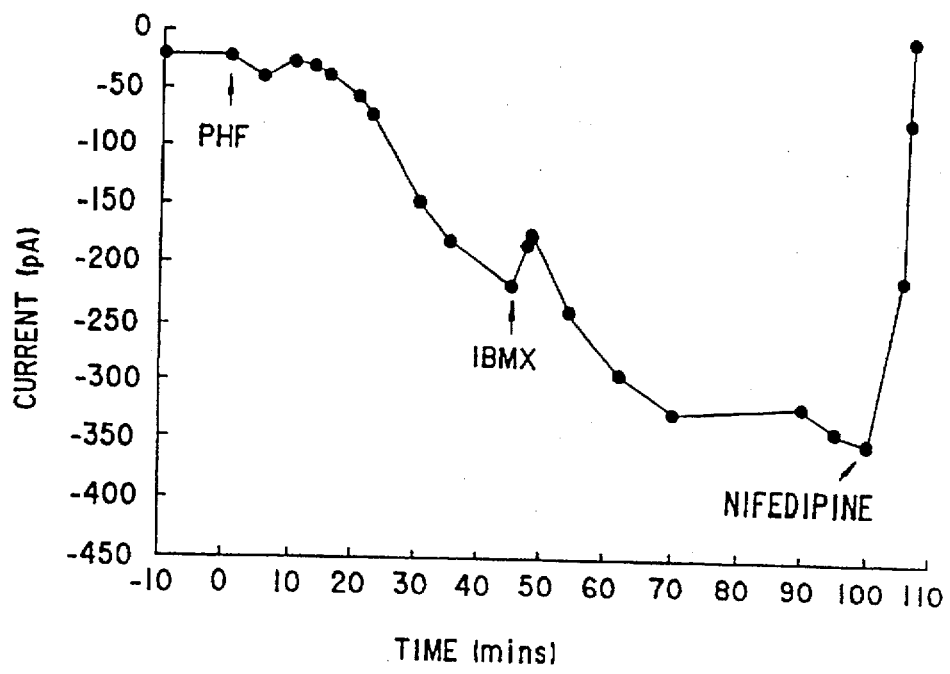
Fig.15

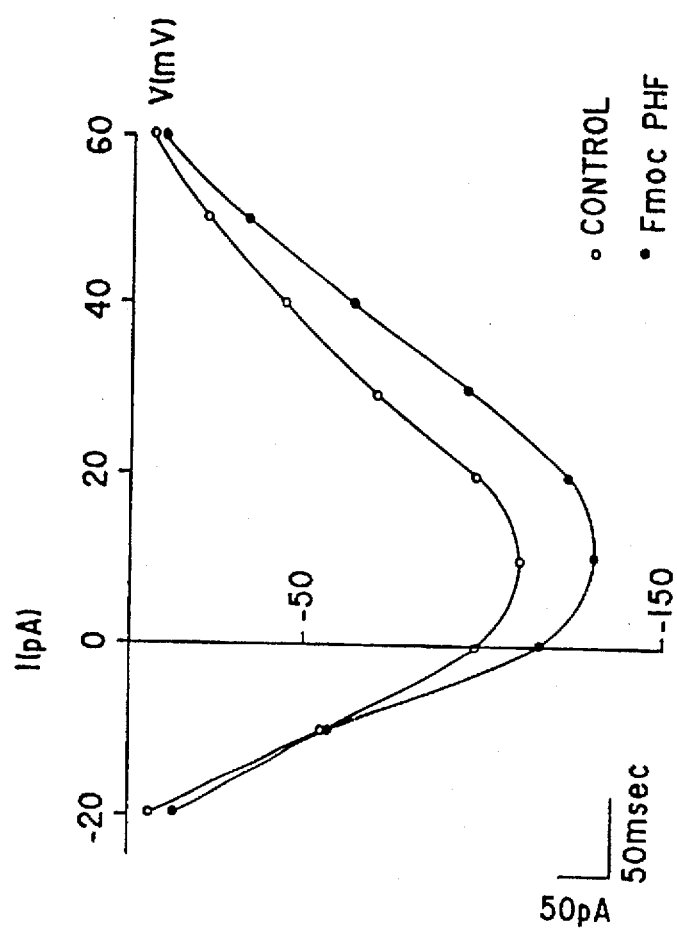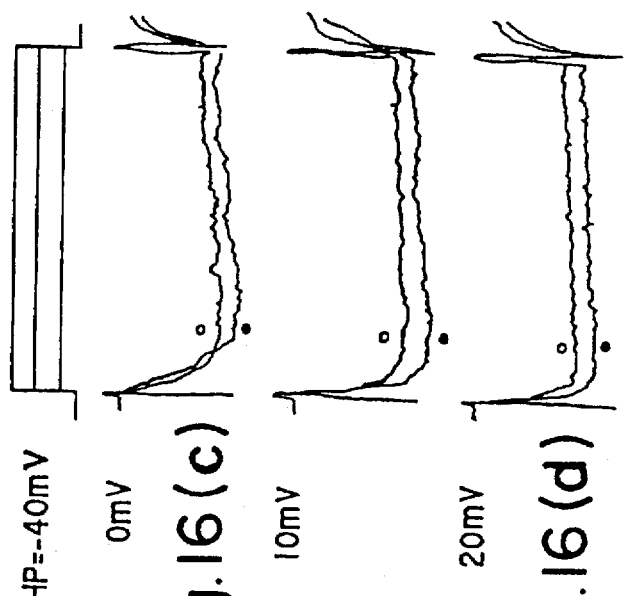

ACTIVE COMPONENT OF PARATHYROID HYPERTENSIVE FACTOR

FIELD OF THE INVENTION

This invention relates to the identification, characterization and synthesis of an active component of parathyroid hypertensive factor which comprises a polypeptide linked to a phosphoglyceride (sometimes referred to as phospholipid). The component exhibits activities substantially similar to parathyroid hypertensive factor and therefore is indicated in the control of extracellular calcium uptake, and is related to hypertension and some other diseases in mammals. Methods for screening patients for the presence of the circulating factor using antibodies against the component are described. Antagonists of the parathyroid hypertensive factor component have been developed and the use of such antagonists in methods of treating patients with diseases which involve intracellular calcium elevation are also described.

BACKGROUND OF THE INVENTION

Hypertension is generally defined as the elevation of the systolic and/or diastolic arterial blood pressure above a nominal value of 140/90 mm Hg. Diseases associated with hypertension include arteriosclerosis, hypertensive renal failure, stroke, congestive heart failure and myocardial infarction. Although numerous methods of treatment have been found to be effective in the reduction of arterial blood pressure, the etiology of essential hypertension remains essentially unknown. A genetic predisposition to hypertension is generally accepted, but the number of different drugs which have been found effective in the treatment of hypertension, and the fact that these drugs seem to operate by eliciting different pharmacological responses, suggests that there may be different primary causes for essential hypertension.

A number of studies have suggested that one or more circulating factors may play a role in the genesis or the maintenance of hypertension [See: Wright et al., A Hypertensive Substance Found in the Blood of Spontaneously Hypertensive Rats; *Life Sci.* 1984; 34:1521–1528; Dahl et al., Humoral Transmission of Hypertension: Evidence from Parabiosis; *Circ. Res.* 1969; 24/25 (Suppl. I):21–23; Greenberg et al., Evidence for Circulating Factors as a Cause of Venous Hypertrophy in Spontaneously Hypertensive Rats; *Am. J. Physiol.* 1981; 241:H421–H430; Tobian et al., A Circulating Humoral Pressor Agent in Dahl S Rats with Salt Hypertension; *Clin. Sci.* 1979; 57:345s–347s; Zidek et al., Humoral Factors in the Pathogenesis of Primary Hypertension; *Klin. Wochenschr.* 1985; 63 (Suppl. II) D:94–96; Hirata et al., Hypertension Producing Factor in the Serum of Hypertensive Dahl Salt-Sensitive Rats; *Hypertension* 1984; 6:709–716]. For example, in parabiosis and cross-circulation experiments, an increase in blood pressure could be induced in normotensive animals by exposure to blood from hypertensive animals. The subcutaneous injection of erythrocyte-associated factor obtained from spontaneously hypertensive rats (SHR) has been shown to induce hypertension in normotensive Wistar-Kyoto (WKY) rats and an increase in blood pressure can be induced in normotensive, salt insensitive Dahl rats by injection of serum from hypertensive, salt-sensitive Dahl rats.

There have also been reports of circulating factors in both hypertensive rats and hypertensive humans which increase intracellular calcium [See: Banos et al., Two Factors Associated with Increased Uptake of Calcium in Platelets from Essential Hypertensive Patients; *Clin. Exp. Hypertens.* 1987; 9:1515–1530; Zidek et al., Effect of Plasma from Hypertensive Subjects on Ca Transport in Permeabilized Human Neutrophils; *Clin. Sci.* 1988; 74:53–56; Linder et al., Effects of a Circulating Factor in Patients with Essential Hypertension on Intracellular Free Calcium in Normal Platelets; *N. Eng. J. Med.* 1987; 316:509–513; Bruschi et al., Cytoplasmic Free Ca is Increased in the Platelets of Spontaneously Hypertensive Rats and Essential Hypertensive Patients; *Clin. Sci.* 1985; 68:179–184; Wright et al., Stimulation of Aortic Tissue Calcium Uptake by an Extract of Spontaneously Hypertensive Rat Erythrocytes Possessing Hypertensive Properties; *Can. J. Physiol. Pharmacol.* 1986; 64:1515–1520]. Since vascular tone is influenced by the level of intracellular calcium, it would seem reasonable to assume—although it has not yet been experimentally shown—that factors which increase blood pressure and factors which increase intracellular calcium may be related. There has been accumulating evidence suggesting the involvement of calcium regulating hormones in some forms of hypertension [See: L. M. Resnick, *Am. J. Med.* 82 (Suppl. 1B), 16 (1987)]. Parathyroid hormone (PTH) is a calcium regulating hormone. Thirty percent or more of essential hypertensive patients fall into a subgroup characterized by increased levels of immunoreactive parathyroid hormone (ir-PTH). [See: Laragh et al., *Kidney Int.* 34, (Suppl. 35), S162 (1988)]. An increase in PTH levels has been reported in SHR rats [See: McCarron et al., *Hypertension* 3 (Suppl. 1), I162 (1981)]and it has been observed that hyperparathyroid patients often exhibit hypertension, the severity of which can, in most cases, be reduced by parathyroidectomy [See: Hellstrom et al., *Brit. J. Urol.* 30, 13 (1958)]. Similar results from parathyroidectomy have also been reported in SHR rats. [See: Schleiffer et al., *Jap. Circ. J.* 45, 1272 (1981)]. Various investigators have suggested that PTH contributes to the development of essential hypertension, although exogenous administration of PTH causes a reduction in blood pressure in mammals and other vertebrates [See: Pang et al., *Gen. Comp. Endocrinol.* 41, 135 (1980)]. This vasodilating action of PTH also has been related to a specific region of the molecule separate from the region mediating hypercalcemic effects [See: Pang et al., *Endocrinology,* 112, 284 (1983)]. PTH has also been shown to inhibit calcium entry into vascular smooth muscle [See: Pang et al., *Life Sci.,* 42, 1395 (1988)] through L-type calcium channels [Wang et al., FEBS, Vol. 282, No. 2, pp.331–334 (1991)]. This paradox is further heightened by the fact that hypertensive patients with increased PTH levels exhibit decreased serum ionized calcium levels [See: Resnick et al., *New Engl. J. Med.,* 309, 888 (1983); Hvarfner et al., *Acta. Med. Scand.,* 219, 461 (1986)]. It would be expected that the serum ionized calcium levels would be elevated if PTH were primarily elevated.

The involvement of the parathyroid gland in essential hypertension has been apparent but existing literature on the action of PTH on the vasculature is not consistent with a causative role for PTH in essential hypertension.

The existence of a circulating factor in the blood of the SHR rat was confirmed by the studies which we reported in *Am. J. Hypertens.,* 2, 26–31 (1989). In these studies, we showed an increase in the blood pressure of WKY and SD rats when plasma from SHR rats was injected into the normotensive rats either by infusion or by bolus injection. In addition, we have shown that the uptake of $_{45}$Ca by sections of the tail artery of a rat, in vitro, increased in a dose-dependent manner as the concentration of SHR plasma was increased in a buffer-based medium. The results of these experiments clearly show that an increase in blood pressure and an increase in calcium uptake in the cells were both dose-dependent on the amount of SHR plasma present and available in the system. Curiously, the onset of both events was delayed, and gradual, whereas known endogenous pressor agents such as norepinephrine, angiotensin II and vasopressin have been observed to increase blood pressure almost immediately and quite rapidly after administration. The known endogenous pressor agents exhibit about a 1–2 minute onset in the increase of blood pressure and increase in calcium uptake in the cells whereas parathyroid hypertensive factor has a 20–30 minute delay before such onset. Another result observed in these studies was that when the infusion of SHR plasma was stopped and substituted with plasma from normotensive rats, the observed blood pressure decreased quite rapidly to the baseline. The decrease observed precluded a simple volume effect. In a related experiment, dialyzed plasma from hypertensive human subjects was infused into normotensive SD rats and shown to produce hypertension. Plasma from these subjects also increased calcium uptake in rat tail arteries in vitro. Dialyzed plasma from normotensive patients produced no significant increase in blood pressure.

The origin of the circulating factor was unknown, but the anecdotal reports that PTH was elevated in hypertensive rats suggested the parathyroid gland as a target of investigation. Parathyroidectomies of SHR rats were found to reduce blood pressure and plasma from the SHR rats which had been parathyroidectomized did not cause elevation of blood pressure in normotensive rats. Conversely, transplantation of parathyroid glands from SHR rats to normotensive Sprague-Dawley (SD) rats resulted in an increase in blood pressure and the appearance of the factor in the plasma, as shown by infusion of the isolated plasma into other normotensive rats. [Pang and Lewanczuk, Amer. J. Hypertens., 2, 898 (1989)].

On the basis of these studies, we concluded that the parathyroid was the origin of the circulating factor and have proposed the name "Parathyroid Hypertensive Factor" or PHF for this substance.

The isolation and purification of a previously unreported circulating factor, having its origin in the parathyroid gland, has been demonstrated in SHR rats and in many humans having essential hypertension and is the subject matter of related patent application Ser. No. 603,745, filed Nov. 21, 1990, which is a continuation-in-part of patent application Ser. No. 327,450, filed Mar. 22, 1989, now abandoned. The disclosure of the related patent applications are incorporated herein by reference for their teachings, including the teachings of purification of parathyroid hypertensive factor.

As described in the aforementioned related patent applications, the factor has been shown to regulate extracellular calcium uptake, and can be inhibited by increases in dietary calcium levels. The factor has been isolated and a method for screening for the factor using antibodies raised against the factor is described. The factor has a molecular weight of approximately 2,700 daltons and has the property of delayed onset of an increase in blood pressure of a normotensive rat when administered thereto, the increase in blood pressure temporally correlating with an increase in extracellular calcium uptake by vascular smooth muscle. From bioassay data, the factor in humans and rats has been found to be substantially similar.

BRIEF SUMMARY OF THE INVENTION

The present invention relates to the identification of an active component of parathyroid hypertensive factor which comprises a polypeptide linked to a phosphoglyceride and has the property of delayed onset of an increase in blood pressure of a normotensive rat when administered thereto, the increase in blood pressure temporally correlating with an increase in extracellular calcium uptake by vascular smooth muscle. Antibodies raised against the component are used in an immunological assay to test for the presence of parathyroid hypertensive factor or portions thereof, the presence being indicative of hypertension or another disease related to an increase in calcium levels. Antagonists of the parathyroid hypertensive factor component have been developed and the use of such antagonists in methods of treating patients with diseases which involve intracellular calcium elevation are also described.

BRIEF DESCRIPTION OF THE DRAWINGS

FIG. 3 shows the effect of pure PHF (0.1 µl SHR plasma equivalent/ml bath medium) on the $[Ca2+]_i$ increment induced by 30 mM KCl in VMSC isolated from rat tail artery. $[Ca^{2+}]_i$ increment in control group is 121.83±31.18 (nM).

FIG. 4 shows LPC significantly augments the increase in intracellular calcium induced by KCl in vascular smooth muscle cells.

FIG. 13 shows the effect of FMOC-PHF (0.01 µ/ml bath medium) on the $[Ca^{2+}]_i$ increment induced by 15 mM KCl in VMSC isolated from rat tail artery.

FIG. 14 shows the time-dependent effect of pure PHF (0.1 μl SHR plasma equivalent/ml bath medium) on L-type $Ca^{2+}$ channel activity in a VMSC isolated from rat tail artery. The left side of this figure shows the original records at the three test pulses. The right side shows control current (I) voltage (V) relationships (•) and that obtained at 35 mins. (■) or 50 mins. (▼) after application of pure PHF (0.1 μl SHR plasma equivalent/ml bath medium). The holding potential was –40 mV.

FIG. 15 shows the effect of IBMX ($5 \times 10^{-5}$M) and nifedipine ($10^{-6}$M) on the L-type $Ca^{2+}$ current activated by pure PHF (0.1 μl SHR plasma equivalent/ml bath medium) in a VMSC isolated from rat tail artery. The time-dependent peak current change was monitored continuously for 105 mins. after application of pure PHF, IBMX and nifedipine at the indicated time.

FIG. 16 shows the effect of FMOC-PHF on calcium channel currents and that FMOC-PHF increased current (downward direction).

DETAILED DESCRIPTION OF THE INVENTION

Figure 1:
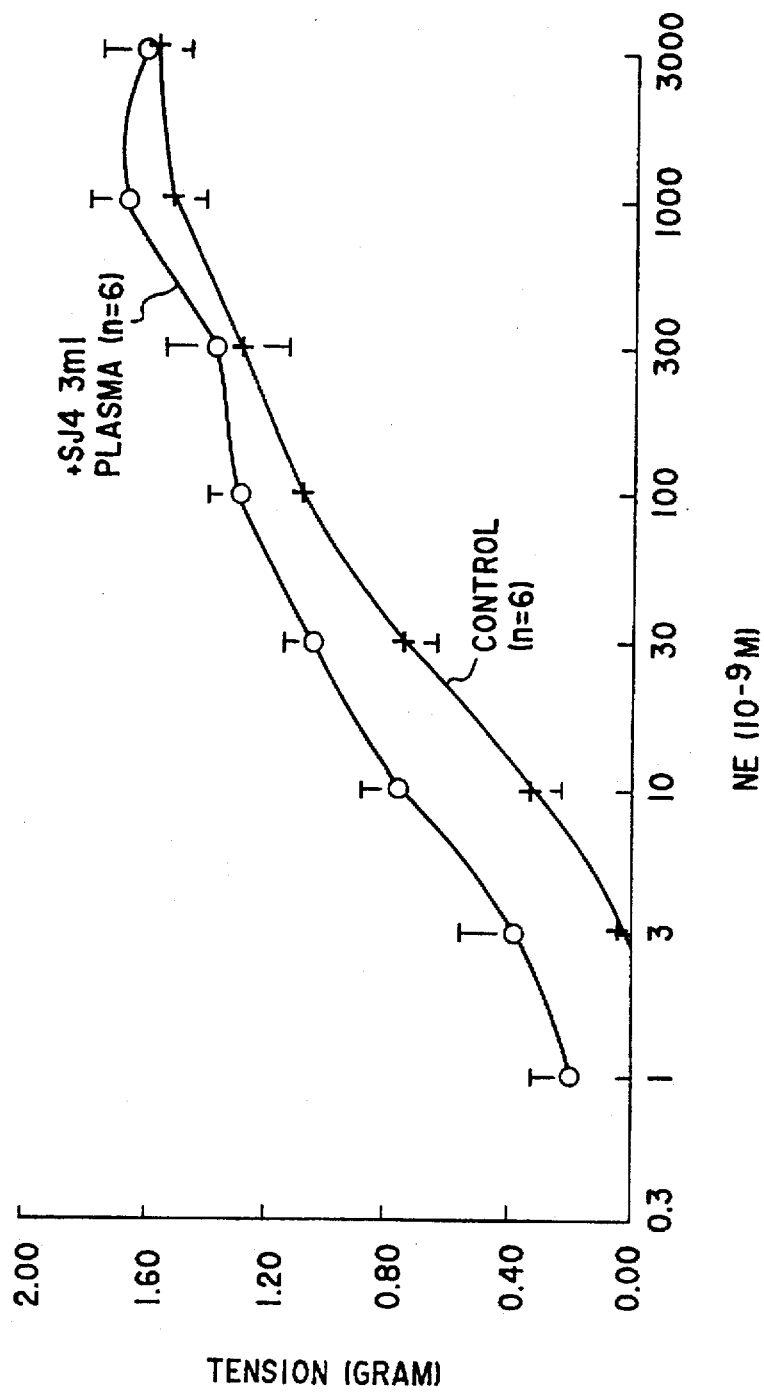
FIG. 1 shows the effect of semi-purified PHF on norepinephrine (NE) induced tension development in rat tail artery. Semi-pure PHF potentiates the NE effect.

The present inventors have identified an active component of parathyroid hypertensive factor which exhibits properties similar to parathyroid hypertensive factor. The component comprises a polypeptide linked to a phosphoglyceride and which has the property of delayed onset of an increase in blood pressure of a normotensive rat when administered thereto, the increase in blood pressure temporally correlating with an increase in extracellular calcium uptake by vascular smooth muscle. That is, when the component is administered to, for instance, a rat, one begins to see a rise in blood pressure at about 20–30 minutes after administration, which peaks out at about one hour. At the same point in time, one also sees an increase in extracellular calcium uptake by vascular smooth muscle cells—that is, uptake peaks out at around one hour.

The polypeptide of the component preferably has from 5–20 amino acid residues and more preferably from 5–10 amino acid residues. The amino acids comprising the polypeptide of the component can be any of those chosen from the group of basic amino acids consisting of Alanine (Ala), Arginine (Arg), Asparagine (Asn), Aspartic acid (Asp), Cysteine (Csy), Glutamine (Gln), Glutamic acid (Glu), Glycine (Gly), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr) and Valine (Val) with the component retaining substantially similar properties to parathyroid hypertensive factor, for example, the property of delayed onset of an increase in blood pressure of a normotensive rat when administered thereto, the increase in blood pressure temporally correlating with an increase in extracellular calcium uptake by vascular smooth muscle. Non-basic amino acids may replace the basic amino acids in the component. Such non-basic amino acids would include for example ornithine, sarcosine, norleucine, N-methylphenylalanine and the like. Preferably the structure of the polypeptide represents Tyr-Ser-Val-Ser-His-Phe-Arg. [SEQ ID NO:1].

The phosphoglyceride of the component may be linked in any position as long as the component retains properties substantially similar to parathyroid hypertensive factor, including the property of delayed onset of an increase in blood pressure of a normotensive rat when administered thereto, the increase in blood pressure temporally correlating with an increase in extracellular calcium uptake by vascular smooth muscle. It is preferred that the linkage be at one of the Serine residues and more preferably, at the Serine residue in position 4 (as depicted in the sequence above). Preferably, the phosphoglyceride is a lysophosphatidic acid or a phosphatidic acid.

The parathyroid hypertensive factor component has a molecular weight between about 1,000 and about 2,700 daltons as measured by mass spectrometry. Preferably the molecular weight is in the range of about 1,000 daltons to about 2,000 daltons and more preferably is about 1,350 daltons. It is noted, however, that there may be additional non-interfering amino acids on either side of the component polypeptide which would make the molecular weight of the component molecule much higher than 2,700.

The parathyroid hypertensive factor component may be bound to a biologically active compound or molecule and this can serve as targeting agent for the transport of biologically active compounds to specified sites within cells, tissues, organs or the like. Examples of biologically active compounds would include hormones, renal drugs, diuretics, neurotransmitters and similar compounds. The biologically active compounds would, for example, be targeted to cells such as vascular smooth muscle, renal and cardiac cells and the like. Methods of binding the biologically active compound or molecule to the component are well known in the art.

Alternatively, the parathyroid hypertensive factor component may be bound to a detectable marker or label which would serve to identify the presence of the component in a biologically sample. Examples of such markers and labels are fluorescein, HRP, biotin and the like. Methods of binding the markers and labels to the component are well known in this art.

In another aspect of the invention, the parathyroid hypertensive factor component has the property of delayed onset of an increase in blood pressure of a normotensive rat when administered thereto, the increase in blood pressure temporally correlating with an increase in extracellular calcium uptake by vascular smooth muscle, has a structure which is different from parathyroid hypertensive factor and has the following structure identified as:

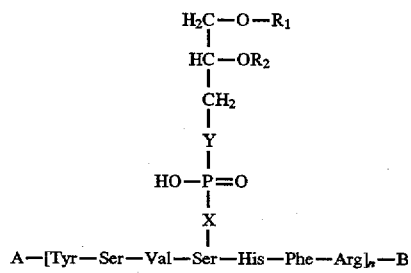

wherein $R_1$ is hydrogen, a $C_1$–$C_{22}$ alkyl, a $C_1$–$C_{22}$ alkenyl or at least one fatty acid group, $R_2$ is as previously defined for $R_1$; each of X and Y are oxygen or sulfur; each of A and B are from 0 to 20 additional amino acids with the proviso that at least one of A and B does not have an amino acid sequence corresponding to that of PHF which has been isolated from a hypertensive individual; and n=1 to 5.

Preferably the variable X and Y of the parathyroid hypertensive component structure are oxygen.

The fatty acid $R_1$ is preferably selected from the group of fatty acids consisting of lauric acid, myristic acid, palmitic acid, stearic acid, arachidic acid, behenic acid, lignoceric acid, palmitoleic acid, oleic acid, linoleic acid, α-linolenic acid, γ-linolenic acid, arachidonic acid, EPA (eicosapentanoic acid) and Nervonic acid. More preferable are oleic acid and stearic acid, and most preferred is oleic acid.

The fatty acid $R_2$ is preferably selected from the group of fatty acids consisting lauric acid, myristic acid, palmitic acid, stearic acid, arachidic acid, behenic acid, lignoceric acid, palmitoleic acid, oleic acid, linoleic acid, α-linolenic acid, γ-linolenic acid, arachidonic acid, EPA and Nervonic acid. More preferable are oleic acid and stearic acid, and most preferred is oleic acid.

The fatty acid groups comprising $R_1$ are preferably from 1 to 10 in number. More preferably, the fatty acid groups are from 1 to 5 in number and most preferred is 1 fatty acid group.

The fatty acid groups comprising $R_2$ are preferably from 1 to 10 in number. More preferably, the fatty acid groups are from 1 to 5 in number and most preferred is 1 fatty acid group.

Most preferred is a parathyroid hypertensive factor component having the property of a delayed onset of an increase in blood pressure of a normotensive rat when administered thereto, the increase in blood pressure temporally correlating with an increase in extracellular calcium uptake by vascular smooth muscle, in a manner similar to naturally occurring PHF which has been purified from a hypertensive individual, and having the following structure identified as:

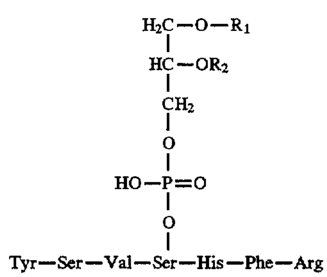

[SEQ ID NO:1]

wherein $R_1$ is hydrogen, a $C_1$–$C_{22}$ alkyl, $C_1$–$C_{22}$ alkenyl or at least one fatty acid group and $R_2$ is as previously defined for $R_1$. The fatty acid $R_1$ is preferably selected from the group of fatty acids consisting of lauric acid, myristic acid, palmitic acid, stearic acid, arachidic acid, behenic acid, lignoceric acid, palmitoleic acid, oleic acid, linoleic acid, α-linolenic acid, γ-linolenic acid, arachidonic acid, EPA and Nervonic acid. More preferable are oleic acid and stearic acid, and most preferred is oleic acid. The fatty acid $R_2$ is preferably selected from the group of fatty acids consisting of lauric acid, myristic acid, palmitic acid, stearic acid, arachidic acid, behenic acid, lignoceric acid, palmitoleic acid, oleic acid, linoleic acid, α-linolenic acid, γ-linolenic acid, arachidonic acid, EPA and Nervonic acid. More preferable are oleic acid and stearic acid, and most preferred is oleic acid. The fatty acid groups forming $R_1$ or $R_2$ may range in number from 1 to 10. Preferably the numbers of fatty acid groups range from 1 to 5. Most preferred is 1 fatty acid group.

The present invention is also directed to a process for producing a parathyroid hypertensive factor component having the property of delayed onset of an increase in blood pressure of a normotensive rat when administered thereto, the increase in blood pressure temporally correlating with an increase in extracellular calcium uptake by vascular smooth muscle, in a manner similar to naturally occurring PHF which has been purified from a hypertensive individual, which has a structure different from parathyroid hypertensive factor and which has the following structure identified as:

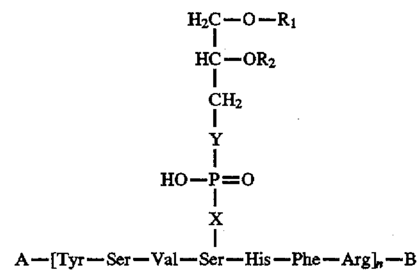

[SEQ ID NO:1]

wherein $R_1$ is hydrogen, a $C_1$–$C_{22}$ alkyl, a $C_{1-C22}$ alkenyl or at least one fatty acid group, $R_2$ is as previously defined for $R_1$ each of X and Y are oxygen or sulfur; each of A and B are from 0 to 20 additional amino acids; and n=1 to 5, comprising the steps of incubating a mixture comprising a polypeptide having the structure A-[Tyr-Ser-Val-Ser-His-Phe-Arg]$_n$-B, wherein A, B and n are as previously defined and a phospholipid with phospholipase D; and recovering the parathyroid hypertensive factor component formed in the previous step.

Preferably the phospholipid is either lysophosphatidic acid or phosphatidic acid.

Preferably in the process for producing the parathyroid hypertensive factor component, the polypeptide is produced by chemical synthesis. The polypeptide may be synthesized in a Conventional peptide synthesizer well known in this art. A representative example of such a synthesizer is the Applied Biosystems peptide synthesizer Model 430A. The procedures for synthesizing peptides using an automated peptide synthesizer are conventional in this art.

Recovery of the component is accomplished by standard purification and separation techniques well known in this art. Representative examples of such techniques include ion exchange and/or reversed-phase HPL chromatography, and TLC.

The present invention also is directed to a process for chemically synthesizing the parathyroid hypertensive factor component. An example of a process for producing a parathyroid hypertensive factor component having the property of delayed onset of an increase in blood pressure of a normotensive rat when administered thereto, said increase in blood pressure temporally correlating with an increase in extracellular calcium uptake by vascular smooth muscle, in a manner similar to naturally occurring PHF which has been purified from a hypertensive individual, which has a structure different from parathyroid hypertensive factor and which has the following structure:

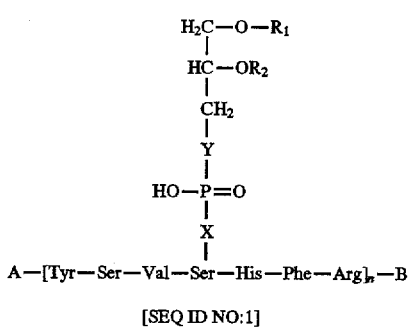

[SEQ ID NO:1]

wherein $R_1$ is hydrogen, a $C_1$-$C_{22}$ alkyl, a $C_1$-$C_{22}$ alkenyl or at least one fatty acid group, $R_2$ is as previously defined for $R_1$ each of X and Y are oxygen or sulfur; each of A and B are from 0 to 20 additional amino acids; and n=1 to 5, comprising the steps of: (a) chemically synthesizing a polypeptide having the structure A-Tyr-Ser-Val-OH, wherein A is as previously defined and purifying said polypeptide; (b) preparing an ester of the polypeptide; (c) adding L-α-lysophosphatidylserine (LPS) to the ester to produce a product having the structure

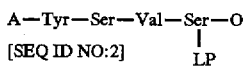

[SEQ ID NO:2]

wherein A is as previously defined and LP is L-α-lysophosphatidyl, and purifying the product; (d) obtaining a product having the structure

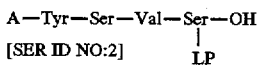

[SER ID NO:2]

by acidifying said product of step (c) and extracting the acidified product and recovering the same by evaporation; (e) preparing an ester of the product of step (d); (f) chemically synthesizing a polypeptide having the structure $NH_2$-His-Phe-Arg-B-OH and purifying the polypeptide; (g) preparing an ester of the polypeptide of step (f) which has the structure $NH_2$-His-Phe-Arg-B-O; and (h) combining the ester of step (e) and the ester of step (g) to produce the parathyroid hypertensive factor component.

Preferably the ester of the polypeptide of step (b) is an N-hydroxysuccinimide ester and is prepared by addition of the polypeptide to a mixture containing dicyclohexylcarbodiimide and dioxane. Moreover, it is preferred that the LPS added to the ester in step (c) is first dissolved in a bicarbonate buffer to form a solution having a pH of 7. In step (d), acidification preferably occurs by addition of sodium citrate to pH of 2.8. Also, the ester of step (e) is preferably an N-hydroxysuccinimide ester and is prepared by addition to the product of Step (d) of a mixture containing dicyclohexylcarbodiimide, dioxane and tetrahydrofuran. In step (h) the ester of step (g) is preferably first dissolved in a bicarbonate buffer to form a solution having a pH of 7 before the solution is combined with the ester of step (e).

Chemical synthesis is carried out in conventional peptide synthesizers well known in this art. For example, synthesis may be carried out in peptide synthesizer model 430A manufactured by Applied Biosystems. Procedures for producing the peptides well known in this art.

Using enzymatically or chemically synthesized parathyroid hypertensive factor component, polyclonal and monoclonal antibodies may be raised against the component and used in any assay for PHF. Procedures for producing polyclonal and monoclonal antibodies are well known in this art.

For example, male Balb/C mice can be immunized by implantation of amino phenolthiol ether discs to which the component has been affixed, according to the procedure of Viamontes et al., *J. Immunol. Meth*, 94, 13–17 (1986). The mice are then boosted with antigen in Freund's incomplete adjuvant at two-week intervals and the antibody titer assayed by enzyme-linked immunosorbent assay (ELISA) using the parathyroid hypertensive factor component of the present invention as the antigen. Detectable amounts of polyclonal antibodies are normally observed within one month and the titer is increased thereafter.

Monoclonal antibodies (MCA) may be prepared from the spleens of polyclonal antibody producing mice.

The required hybridoma and MCA may be obtained using the method of Langone and Van Vunakis, "Methods in Enzymology", 121, 1–947 (1986), using such modifications as are known to skilled practitioners in this art.

The method of detection using polyclonal and/or monoclonal antibodies is not specifically limited and includes radioimmunoassay, enzyme immunoassay, enzyme-linked immunosorbent assays, and assay systems based on the formation of an immunoprecipitate.

Preferably, a method for detecting the presence of parathyroid hypertensive factor or a portion thereof (including the active component) would comprise the steps of raising polyclonal antibodies in an animal (mammal or bird) by injecting a solution containing the parathyroid hypertensive factor component of the present invention into the animal; collecting serum containing polyclonal antibodies raised against the parathyroid hypertensive factor component; screening a sample which may contain parathyroid hypertensive factor or an antigenic portion thereof by an immunoassay method using the polyclonal antibodies; and detecting the presence of the PHF or its antigenic portions in the sample.

The immunoassay method for detecting the presence of parathyroid hypertensive factor or a portion thereof is preferably an enzyme linked immunoassay, an enzyme linked immunosorbent assay or an immunoprecipitation assay.

The sample may be a biological sample. Examples of the sample would include serum, plasma, urine, tissue, cells and the like.

In the aforementioned method, it is preferred that the component have the following structure identified as:

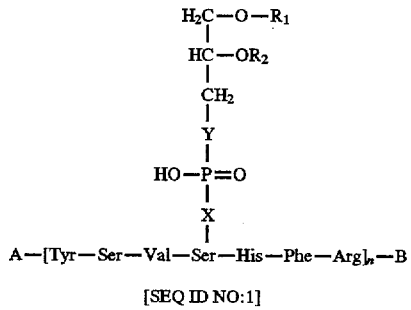

[SEQ ID NO:1]

wherein $R_1$ is hydrogen, a $C_1$-$C_{22}$ alkyl, a $C_1$-$C_{22}$ alkenyl or is at least one fatty acid group, $R_2$ is as previously defined for $R_1$; each of X and Y are oxygen or sulfur; each of A and B are from 0 to 20 additional amino acids with the proviso that at least one of A and B does not have an amino acid sequence corresponding to that of PHF which has been isolated from a hypertensive individual; and n=1 to 5, and more preferably:

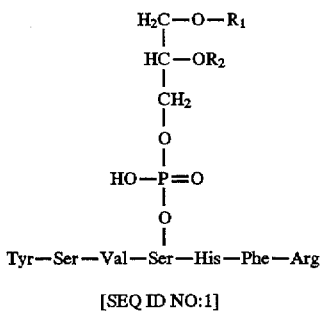

[SEQ ID NO:1]

wherein $R_1$ is hydrogen, $C_1$–$C_{22}$ alkyl, $C_1$–$C_{22}$ alkenyl or at least one fatty acid group and $R_2$ is as previously defined for $R_1$. The fatty acid $R_1$ and $R_2$ are preferably selected from the group of fatty acids consisting of lauric acid, myristic acid, palmitic acid, stearic acid, arachidic acid, behenic acid, lignoceric acid, palmitoleic acid, oleic acid, linoleic acid, α-linolenic acid, γ-linolenic acid, arachidonic acid, EPA and Nervonic acid. More preferable are oleic acid and stearic acid, and most preferred is oleic acid.

In yet another preferred embodiment, a method for the identification of parathyroid hypertensive factor or a portion thereof in a patient would comprise the steps of raising antibodies to the parathyroid hypertensive factor component of the present invention by injecting said component into an animal (mammal or bird); isolating antibody-secreting B-lymphocytes from the immunized animal; fusing the antibody-secreting B-lymphocytes with myeloma cells to form hybridomas; selecting and cloning the hybridomas which secrete parathyroid hypertensive factor component antibody; propagating the antibody-secreting hybridomas; isolating a monoclonal antibody from the hybridomas; and screening a sample which may contain parathyroid hypertensive factor or its portions by an immunoassay method using the monoclonal antibodies.

Again, the immunoassay method may be an enzyme linked immunoassay, an enzyme linked immunosorbent assay, or an immunoprecipitation assay.

The sample is preferably a biological sample. For example, the sample could include serum, plasma, urine, tissue, cells and the like. The patient may be a mammal or a bird and is preferably human.

In the aforementioned method, it is preferred that the component have the following structure identified as:

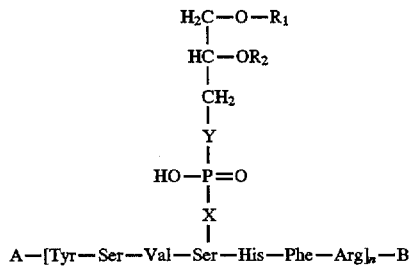

[SEQ ID NO:1]

wherein $R_1$ is hydrogen, $C_1$–$C_{22}$ alkyl, a $C_1$–$C_{22}$ alkenyl or at least one fatty acid group, $R_2$ is as previously defined for $R_1$; each of X and Y are oxygen or sulfur; each of A and B are from 0 to 20 additional amino acids with the proviso that at least one of A and B does not have an amino acid sequence corresponding to that of PHF which has been isolated from a hypertensive individual; and n=1 to 5 and more preferably:

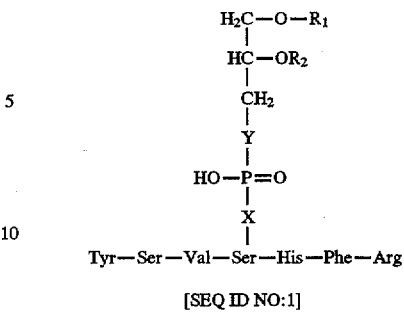

[SEQ ID NO:1]

wherein $R_1$ is hydrogen, $C_1$–$C_{22}$ alkyl, $C_1$–$C_{22}$ alkenyl or at least one fatty acid group and $R_2$ is as previously defined for $R_1$. The fatty acid $R_1$ and $R_2$ are preferably selected from the group of fatty acids consisting of lauric acid, myristic acid, palmitic acid, stearic acid, arachidic acid, behenic acid, lignoceric acid, palmitoleic acid, oleic acid, linoleic acid, α-linolenic acid, γ-linolenic acid, arachidonic acid, EPA and Nervonic acid. More preferable are oleic acid and stearic acid, and most preferred is oleic acid.

A particularly desirable embodiment of such an assay system would be in the form of a diagnostic kit which could be used in a physician's office or a clinic, in the absence of sophisticated analytical instruments. Such methodology has been used for the detection of hormones and other immunoreactive substances in body fluids. One example is a commercially available kit for the detection of early pregnancy. PHF or portions thereof could, therefore, be qualitatively or quantitatively detected by the use of such methods.

Therefore, the present invention also provides for a kit for the detection of parathyroid hypertensive factor or an immunologically reactive portion thereof in an animal, comprising, in a single package an antibody to the parathyroid hypertensive factor component bound to a solid phase; a secondary antibody to anti-parathyroid hypertensive factor component antibody labeled with an enzyme; a substrate for said enzyme label on said secondary antibody; and standard solutions of parathyroid hypertensive factor or a component or portion thereof.

A further kit for the detection of parathyroid hypertensive factor or a portion thereof in an animal is provided which comprises, in a single package, an antibody to the parathyroid hypertensive factor component; a solid phase upon which said antibody attaches; and a standard solution of parathyroid hypertensive factor or a portion thereof.

In both of the above mentioned kits, the preferred component has the following structure:

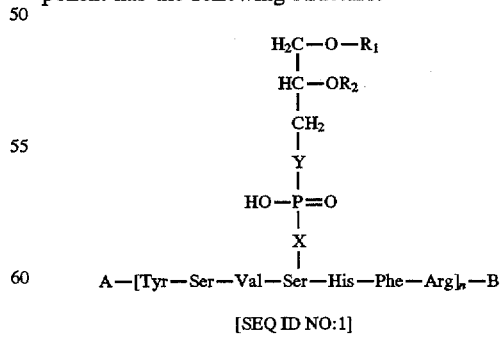

[SEQ ID NO:1]

wherein $R_1$ is hydrogen, a $C_1$–$C_{22}$ alkyl, a $C_1$–$C_{22}$ alkenyl or at least one fatty acid group, $R_2$ is as previously defined for $R_1$; each of X and Y are oxygen or sulfur; each of A and B are from 0 to 20 additional amino acids with the proviso that at least one of A and B does not have an amino acid sequence corresponding to that of PHF which has been isolated from a hypertensive individual; and n=1 to 5 more preferably:
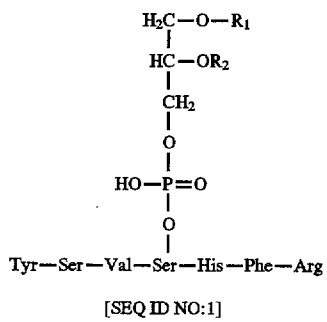
[SEQ ID NO:1]

wherein $R_1$ is hydrogen, $C_1$–$C_{22}$ alkyl, $C_1$–$C_{22}$ alkenyl or at least one fatty acid group and $R_2$ is previously defined for $R_1$. The fatty acid $R_1$ and $R_2$ are preferably selected from the group of fatty acids consisting of lauric acid, myristic acid, palmitic acid, stearic acid, arachidic acid, behenic acid, lignoceric acid, palmitoleic acid, oleic acid, linoleic acid, α-linolenic acid, γ-linolenic acid, arachidonic acid, EPA and Nervonic acid. More preferable are oleic acid and stearic acid, and most preferred is oleic acid.

The present invention is also directed to antagonists of the parathyroid hypertensive factor. While not being bound to any theory, it is believed that the parathyroid hypertensive factor consist of two parts: the activation part (phospholipid part); and the recognition or binding part (peptide part). Again, it is believed that the phospholipid plays a role in allowing transport of the peptide through cell membrane to reach a receptor site where binding of the peptide occurs. By altering the linkage of the phospholipid at the binding site of serine in position 4, a parathyroid hypertensive factor antagonist can be produced. It is believed that the antagonists bind to the parathyroid hypertensive factor site but do not activate parathyroid hypertensive factor activity and thus can further prevent the action of authentic parathyroid hypertensive factor.

Antagonist of the present invention preferably have the following structure

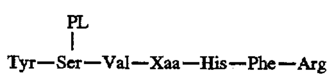

[SEQ ID NO:3]

wherein Xaa is any amino acid other than Serine and PL is a phospholipid. Preferably, the phospholipid is either lysophosphatidic acid or phosphatidic acid. More preferably, Xaa is selected from the group of amino acids consisting of lysine, tyrosine and leucine.

As based on the above figure, other antagonists would include analogs which would bind to receptor or binding sites in the target tissue but would elicit the biological actions. According to the hypothesis that the phospholipids may be involved in the activation of biological actions, its position of linkage with the peptide may be important. While our example shows that linkage to serine of position 4 is required for biological activity and to serine 2 for antagonistic activity, it is therefor possible that linkage in other positions of the peptide of 2–20 amino acids may also result in the formation of antagonists. Since the peptide and the phospholipids must maintain a certain tertiary structure for biological activity, modification of the peptide sequence may produce such tertiary changes that the binding part may not be effected but the phospholipid may be spatially moved and the analogues may become antagonists. Furthermore, if the phospholipid is as important as the activation part of the molecule, its composition may affect its ability to produce the biological response. By changing the composition of the fatty acids and the addition of the fatty acids in the second carbon of the glycerol backbone, antagonists may be produced. In summary, while not being restricted to these approaches, antagonists to the parathyroid hypertensive factor may be designed by (1) having the phospholipid linked to various positions on the peptide, (2) altering the peptide sequence, (3) changing the phospholipid composition and (4) others that may allow the molecule to bind but not to activate the biological pathway leading to the hypertensive response.

The antagonists of the present invention can be used in the treatment of hypertension and other diseases related to intracellular calcium elevation (e.g., non-insulin-dependent diabetes mellitus; atherosclerosis; congestive heart failure; cancer, including breast, colon, kidney and leukemia; inflammatory bowel disease and asthma).

The antagonists of the present invention may be administered to a warm-blooded mammal in need thereof, particularly a human, by parenteral, topical, oral, rectal administration or by inhalation. The antagonists may be conventionally formulated in parenteral or oral dosage form compounding about 1 to about 200 mg per unit of dosage with a conventional vehicle, excipient, binder, preservative, stabilizer, color, agent or the like as called for by accepted pharmaceutical practice.

For parenteral administration, a 1 to 10 ml intravenous, intramuscular or subcutaneous injection would be given one to four times daily. The injection would contain an antagonist of the present invention in an aqueous isotonic sterile solution or suspension optionally with a preservative such as phenol or a solubilizing agent such as ethylenediaminetetraacetic acid (EDTA). Among the acceptable vehicles and solvents that may be employed are water, Ringer's solution and isotonic sodium chloride solution. In addition, sterile, fixed oils are conventionally employed as a solvent or suspending medium. Synthetic monoglycerides, diglycerides, fatty acids (such as oleic acid) find use as fixed oils in the preparation of injectables.

For rectal administration, the antagonists of the present invention can be prepared in the form of suppositories by mixing with a suitable non-irritating excipient such as cocoa butter or polyethylene glycols.

For topical use, the antagonists of the present invention can be prepared in the form of ointments, jellies, solutions, suspensions or dermal adhesive patches.

In a powdered aerosol, antagonists of the present invention may be administered by a Spinhaler turbo-inhaler device obtained from Fisons Corporation of Bedford, Massachusetts, at a rate of about 0.1 to 50 mg per capsule, 1 to 8 capsules being administered daily for an average human. In a liquid aerosol, the compounds of the present invention are administered at the rate of about 100 to 1000 micrograms per "puff" or activated release of a standard volume of propellant. The liquid aerosol would be given at the rate of 1 to 8 "puffs" per day with variation in dosages due to the severity of the conditions being treated, the weight of the patient and the particle size distribution of the aerosol. A fluorinated hydrocarbon or isobutane find use as propellants for liquid aerosols.

Daily doses are in the range of about 0.01 to about 200 mg per kg of body weight, depending on the activity of the specific compound, the age, weight, sex and conditions of the subject to be treated, the type and severity of the disease, the frequency and route of administration. As would be well known, the amount of active ingredient that may be combined with the carried materials to produce a single dosage will vary depending upon the host treated and the particular mode of administration.

In addition to identification of essential hypertension, the existence of an active PHF component and assays for PHF are applicable to the study and treatment of other diseases which may or may not necessarily include hypertension as a primary symptom. For example, non-insulin dependent diabetes frequently are hypertensive. Conversely, hypertensives frequently show an impaired glucose tolerance. In both circumstances, increased intracellular free calcium has been observed. PHF has 5 been detected in the plasma of Ob/Ob mice, which are obese, hypertensive and have non-insulin dependent diabetes. The PHF from these mice has been isolated from the sera in the same subfraction as PHF from SHR rats. Detection of PHF may be useful in diagnosis of non-insulin dependent diabetes (NIDDM) and may open a new area of research into the role of PHF in NIDDM.

Some forms of cancer are characterized by an increase in intracellar free calcium [see: Okazaki et al., *Canc. Res.*, 46 (12 Pt 1), 6059–6063 (1986); Lipton and Morris, *Canc. Chemother. Pharmacol.*, 18(1), 17–20 (1986); Chien and Warren, *Canc. Res.*, 46(11), 5706–5714; Shirakawa et al., *Canc. Rest.*, 46(2), 658–661 (1986); and Meyer, *J. Hypertens.*, 5 (suppl. 4), S3–S4 (1987)]. Parathyroid activation also has been associated with certain types of cancer [see: Palmer et al., *Am. J. Epidemiol.*, 127(5), 1031–1040 (1988) and Feig and Gottesman, *Cancer*, 60(3), 429–432 (1987)]. As PHF or portions thereof are of parathyroid origin, and as preliminary data suggests that PHF can increase intracellular calcium levels, PHF or portions thereof may be implicated in these and other forms of cancer. Thus, screening for PHF may be valuable in understanding the etiology of these cancers as well as in developing detection methods and therapeutic regimens.

The following examples illustrate this invention but are not limiting thereof. Various modifications may be apparent to those skilled in the art without deviating from the scope of this invention.

EXAMPLE 1

Extraction of Plasma with Chloroform/Methanol

Male rats of the SHR strains were decapitated and exsanguinated and the pooled blood was heparinized (100 IU/ml) and centrifuged at 3K×g for 10 min. at 4° C. Plasma from SHR rats was dialyzed against distilled water overnight (1,000 mwco) and filtered using an Amicon ultra-filtration cell (5,000 mwco).

The plasma was then homogenized with 20 volumes of chloroform:methanol (2:1 v/v) and allowed to sit overnight at 4 degrees C. The organic phase was collected and washed with 5 volumes of 0.1M NaCl. The extract was then concentrated by rotary evaporation at 40°–50° C. and freeze dried. A BCA assay was performed to determine the amount of protein in the sample.

SD rats were anesthetized using Na pentobarbital, (50 mg/kg, i.p.) and catheters were inserted in the jugular vein for injection of plasma and drugs and in the carotid artery for measurement of b.p.

The chloroform methanol extract of SHR plasma was redissolved in saline and administered by bolus injection.

The blood pressure increased slowly, in a manner similar to PHF. The maximum increase in blood pressure of 16.4±3.5 mmHg occurred at 45 to 50 min. (n=5). The test indicates that PHF is extracted by chloroform:methanol.

EXAMPLE 2

Bioassay of Chloroform/Methanol Extract from Gland Culture Medium

Thyroparathyroid glands were excised from SHR rats and cultured for up to 7 days in Hank's medium (Gibco), with the media changed daily. The production of PHF may be stimulated by reduction of calcium from the medium. Pooled media, after dialysis and filtration analogous to the treatment of plasma samples, was lyophilized.

Gland culture medium, dialyzed, filtered and lyophilized as described in the previous example, was first extracted with 20 volumes of ether, followed by 10 volumes of chloroform methanol (4:1). The two extracts and the remaining aqueous phase were lyophilized and reconstituted in saline for a blood pressure bioassay as described in Example 1 and the following results obtained:

| SAMPLE | PHF (incr. in BP mmHg) |
| --- | --- |
| Ether extract: | 2.4 |
| chloroform: methanol extract | 9.8* |
| Aqueous phase | 4.6 |

*indicates PHF activity

EXAMPLE 3

Determination of Structure of PHF Component

A. Base Hydrolysis

The procedure was performed according to the protocol of Schwarz, Bumpus & Page I. H., J. Am. Chem. Soc. Vol 79, p.5697 (1957) A plasma sample from SHR rats (equal to 20 ml original plasma) was dialyzed, filtered and lyophilized according to the previous Example. The sample was dissolved in 10 ml 0.15N NaOH. The sample was then incubated at room temperature for 3 hr and then neutralized with 0.15N HCl. A control was prepared in a similar manner except that no plasma sample was included in the incubation.

A bioassay was performed as described in Example 1 and the results are shown below:

Control: BP=−0.75±2.2 mm Hg (n=4)

Plasma containing sample:BP=−0.5±5.7 mm Hg (n=6) (no PHF)

The test demonstrates that PHF activity is sensitive to degradation by base hydrolysis. This suggests the presence of an ester linkage in the molecule which is critical for biological activity.

B. Acid Hydrolysis

A plasma sample from SHR rats (equivalent to 20 ml original plasma) was dialyzed, filtered and lyophilized according to Example 1. The sample was dissolved in 10 ml 0.1N HCl and then incubated at room temperature for 3 hr. The sample was then neutralized with 0.1N NaOH. A control was prepared in a similar manner except that no plasma sample was included in the incubation.

A bioassay was performed as described in Example 1 and the results are shown below:

Control: BP=−4.2±1.5 mm Hg (n=6)

Plasma containing sample: BP=+20.5±3.3 mm Hg (n=4)
* PHF

The test demonstrates that PHF activity is not sensitive to weak acid hydrolysis.

C. Disulfide Reduction and Alkylation

The procedure was conducted according to the protocol as described in Waxdahl et al., *Biochemistry*, Vol.7 (1959). A buffer of 5M guanidine hydrochloride, 0.5M Tris, 2 mM EDTA, with a pH of 8.1 was prepared.

A plasma sample from SHR rats is dialyzed, filtered and lyophilized according to Example 1 and dissolved in 1 ml of the buffer. The tube is flushed with $N_2$, and incubated for 30 minutes at 50° C. DTT (44.2 mg) is added, and the tube is again flushed with $N_2$. The resulting solution is incubated at 50° C. for 4 hr and iodoacetic acid is added in an amount of 111 mg. The pH of the solution is adjusted to 8.1 by appropriate addition of 1M KOH, and incubated for 20 minutes at room temperature. Molar ratios were DTT/plasma fraction=300/1 and DTT/Iodoacetic acid=½.

The sample is then dialyzed against ice-cold water and the pH adjusted to 7.0 with HCl and diluted to the original volume of plasma. A control was prepared in a similar manner except that the plasma sample was omitted.

A bioassay was performed as described in Example 1 and the results are shown below:

Control: BP=+3.5±2.5 mm Hg (n=4)
Plasma containing sample: BP=+18.0±5.5 mm Hg (n=6)
*PHF The test shows that PHF activity was not inactivated by reduction and alkylation, suggesting that there is no disulfide linkage in the structure which is crucial for biological activity. Instead the reaction seemed to increase the activity of the sample, suggesting that the reaction may have stabilized the molecule to degradation.

D. Degradation Assay—Phospholipase C

A buffer comprising 50 mM glycine as a buffer, having a pH of 8.0 and containing 1 mM $ZnCl_2$ is prepared. A plasma sample from SHR rats was dialyzed, filtered and lyophilized according to Example 1 and dissolved in the buffer (6 mg/ml). The phospholipase C enzyme from *Bacillus cereus* (commercially available through Boehringer Mannheim) is dissolved in the buffer solution (4000 units/ml) and 1 ml sample plus 0.1 ml enzyme is incubated at 37° C. for 4 hrs. The sample is then heated to 96° C. for 5 min.

Controls were prepared as follows:
Control 1: PLC and buffer;
Control 2: Buffer; and
Control 3: plasma sample and buffer.

A bioassay was conducted as in Example 1. The results of the assay are as follows:

| Total Reaction | Control 3 | Control 1 | Control 2 |
| --- | --- | --- | --- |
| −2.8 mmHg | 9.8 mmHg | −2.0 mmHg | −5.0 mmHg |

The 9.8 mmHg result indicates positive parathyroid hypertensive factor activity. PHF activity was inactivated by phospholipase C (PLC).

E. Degradation Assay—Phospholipase $A_2$

A buffer comprising 50 mM Tris as a buffer, having a pH of 7.4 and containing 20 mM $CaCl_2$, and 100 mM NaCl is prepared. A plasma sample from SHR rats was dialyzed, filtered and lyophilized according to Example 1 and dissolved in the buffer (6 mg/ml). The phospholipase $A_2$ enzyme from *Naja mocambique mocambique* (commercially available through Sigma Chemical Co.) is dissolved in the buffer (1500 units/ml) and 1 ml sample plus 0.1 ml enzyme is incubated at 37° C. for 2 hrs. The sample is then heated to 96° C. for 5 min.

Controls were prepared as follows:
Control 1: plasma sample and buffers; and
Control 2: Enzyme and buffer.

A bioassay was conducted as in Example 1. The results of the assay are as follows:

| Total Reaction | Control 1 | Control 1 |
| --- | --- | --- |
| 14.0 mmHg | 8.8 mmHg | 3.3 mmHg |

The 8.8 mmHg result indictes positive parathyroid hypertensive factor activity. PHF activity was not inactivated by phospholipase $A_2$.

F. Degradation Assay—Phospholipase D

The procedure is conducted in accordance with the protocol established in Bergmeyere et al. (1983) in *Methods of Enzymatic Analysis* (Bergmeyer ed.) 3rd ed, vol. 2, pp. 288–291. The phospholipase D enzyme is obtained from cabbage and is commercially available through Boehringer Mannheim.

A buffer containing 50 mM Tris/HCl at a pH of 7.8 containing 0.2% Triton X-100 is prepared. A plasma sample from SHR rats was dialyzed, filtered and lyophilized according to Example 1 and dissolved in 2 ml of the buffer. Phospholipase D in an amount of 1 mg/ml is added to the solution which is then incubated at 37° C. for 20 minutes.

Controls were prepared as follows:
Control 1: Phospholipase D and buffer
Control 2: Buffer
Control 3: Plasma sample and buffer A bioassay was conducted as in Example 1. The results of the assay are as follows:

| Total Reaction | Control 3 | Control 1 | Control 2 |
| --- | --- | --- | --- |
| −4.6 mmHg | 11.5 mmHg | 2.7 mmHg | 0.6 mmHg |

The result of 11.5 mmHg indicates a positive parathyroid hypertensive factor activity. PHF activity was inactivated by phospholipase D.

G. Degradation Assay—Trypsin

The assay is conducted according to the procedures described in *Methods in Enzymology*, Vol. 182, pp. 602–613 (1990) and *J. Biol. Chem.*, Vol. 240, p. 1619 (1965).

Some trypsin (from bovine pancreas; Boehringer Mannheim, Montreal PQ) was first treated with TPCK (N-tosyl-phenylalanine chloromethyl ketone) to inactivate any chymotrypsin which might be contaminating the preparation. Trypsin (60 mg) was dissolved in 20 ml of 1 mM $CaCl_2$ and the pH was adjusted with the addition of NaOH to obtain a pH of 7. TPCK (1 mg) was dissolved in 0.1 ml ethanol and added to the trypsin preparation dropwise at room temperature. The solution was stirred for 5 hr and the pH adjusted with the addition of HCl to 3.0. The solution was then dialyzed in water for 24 hrs. at 4° C. Thereafter, the dialyzed solution was freeze dried and weighed.

A plasma sample (equivalent to 20 ml of original plasma) from SHR rats was dialyzed, filtered and lyophilized according to Example 1 and dissolved in 2 ml of a buffer made up of 50 mM $NH_4HCO_3$, pH 7.5. Trypsin-TPCK in an amount of 36 µg is added and the solution is incubated at 37° C. for 18 hr. The sample is then heated to 96° C. for 5 min and the pH adjusted to 7.0.

Controls were prepared as follows using the above described procedures:

Control 1: Buffer only

Control 2: Buffer and Trypsin-TPCK

Control 3: Buffer and plasma sample

A bioassay was performed as described in Example 1 and the results are shown below:

Control 1 BP=−8.4±5.3 mm Hg (n=5)

Control 2 BP=±6.1+2.9 mm Hg (n=6)

Control 3 BP=±9.0+5.3 mm Hg (n=5)

Total Reaction BP=0±3.5 (n=6)

It was concluded that PHF activity is sensitive to inhibition by trypsin, but not to inactivation by heating. This would suggest that PHF contains a peptide-like structure.

H. Degradation Assay—Carboxypeptidase A

This assay is conducted according to the protocol of *Meth. Enzymol. XI* pp. 155–166, and *J. Biol. Chem.*, Vol. 237, pp. 1851–1855 (1962).

A buffer containing 0.1M ammonium bicarbonate (pH 8.5) is prepared. A plasma sample from SHR rats was dialyzed, filtered and lyophilized according to Example 1 and dissolved in 2 ml of buffer. Carboxypeptidase A is added (0.1 mg) (Weight ratio: Carboxypeptidase A/plasma =1/70). The sample is incubated at 37° C. for 4 hrs and the reaction halted by acidification to a pH of 4 by addition of an appropriate amount of acetic acid. The sample is then heated to 96° C. for 5 min.

A control was prepared using the above procedures by omission of enzyme from the sample.

A bioassay was performed as described in Example 1. The results of the assay are total reaction=−1.6 mmHg and for the control 15.5 mmHg. The result of 15.5 mmHg indicates positive parathyroid hypertensive factor activity. It was concluded that PHF activity is sensitive to carboxypeptidase A, suggesting that it contains a peptide-like structure.

I, Degradation Assay—Chymotrypsin

This assay is conducted according to the protocol of *Methods in Enzymology*, Vol. 182 pp. 613–626 (1990).

A buffer containing 50 mM $NH_4HCO_3$, 0.4M NaCl, 2 mM $MgCl_2$ is prepared. A plasma sample from SHR rats was dialyzed, filtered and lyophilized according to Example 1 and dissolved in 2 ml of buffer. Chymotrypsin $A_4$ is added (Weight ratio: Chymotrypsin/plasma=1/50). The sample is incubated at 0° C. for 15 min and heated to 96° C. for 5 min.

Controls were prepared using the above described procedures by omission of enzyme from the sample.

A bioassay was performed as described in Example 1 and the results are shown below:

Control: BP=+10.6±2.3 mm Hg (n=6)

Total Reaction: BP=−2.0±1.2 mm Hg (n=5)

The assay indicates that PHF activity is sensitive to inactivation by chymotrypsin, and that PHF contains a peptide-like structure.

EXAMPLE 4

In vitro enzymatic synthesis of PHF Component

Five (5) mg. of four seven-amino acid peptides (denoted CS2129 having the structure Y-S-V-S-H-F-R[SEQ ID NO.1], CS2130 having the structure Y-S-V-K-H-F-R[SEQ ID NO.6], CS2131 having the structure Y-S-V-Y-H-F-R [SEQ ID NO.7], and CS2132 having the structure Y-S-V-L-H-F-R[SEQ ID NO.8], all from Alberta Peptide Institute) and a liqid mixture of Table 1 (Avanti Polar Lipids, 0.5 to 1.5 mg) were incubated with phospholipase D (1 mg) in 50 mM Tris buffer, pH 7.8, in a final volume of 1 ml. Simultaneously the appropriate controls were also incubated. (A control peptide used is NSP (non-specific peptide) having the structure G-L-N-R-K-Y-L-V[SEQ ID NO.9]). Incubation was at 37° C. for a period of 1 hour. The reaction was terminated at the appropriate time by heating the sample to 95° C. for 5 min.

The samples were bioassayed according to the procedure of Example 1. The blood pressure bioassay results are shown in Table 1. In the bioassay for PHF like (agonist) activity (Table 1), lysophosphatidic acid with oleic or palmitic acid gave the best biological activity. Also, phosphatidic acid with dioleic acid gave some activity. The other analog peptides did not give biological activity.

EXAMPLE 5

Chemical Synthesis of PHF Component

Unless otherwise stated, chemicals and solvents were reagent grade. Diisopropylethylamine (DIEA), dichloromethane, anisole and trifluoroacetic acid (TFA) were redistilled prior to use. N,N-dimethylformamide (DMF) was stored over 4A molecular sieves prior to use. All the above solvents were obtained from General Intermediates of Canada. HPLC-grade water, methanol and acetonitrile were obtained from J. T. Baker Chemical (Phillipsburg, N.J.). Dicyclohexylcarbodimide (DCC) and 1-hydroxybenzotriazole (HOBT) were obtained from Applied Biosystems (Foster City, Calif.). 1,2-ethanedithiol (EDT) and N-hydroxysuccinimide (NHS) were purchased from Aldrich Chemical (Milwaukee, Wis.), and acetic anhydride was obtained from Fisher Scientific (Fairlawn, N.J.). N-Boc-L-valine and N-α-Boc-$N_g$-p-tosyl-L-arginine-PAM resins (1% divinylbenzene, 0.5 mmol/gm substitution), tert-butyloxycarbonyl (BOC) and 9-fluoronylmethyloxycarbonyl (FMOC) amino acids were purchased from Bachem Fine Chemicals (Torrance, Calif.). L-α-lysophophatidylserine (1-stearoyl-sn-glycero-3-phospho-O-serine), sodium salt was purchased from Avanti Polar Lipids (Alabaster, Ala.).

Peptide synthesis was carried out on an Applied Biosystems peptide synthesizer Model 430A. The analytical HPLC instrument consisted of a Hewlett Packard 1090M liquid chromatograph (Avondale, PA) equipped with 250 ml autosampler and diode-array detection system coupled to HP 9000 series 300 computer, HP 9153C disc drive, HP 2225A Think Jet printer and HP 7440A Color Pro Plotter.

Purification of crude peptides was carried out on a Gilson preparative HPLC system (Middleton, Wis.) consisting of two Model 303 metering pumps each with Model 25.SC pump heads, a Model 803 manometric module, Model 811 dynamic mixer with 23 ml preparative chamber and a Model HM variable wavelength detector. Peptides were injected with a Rheodyne Model 7125 sample injector (Cotati, Calif.). Pump parameters were controlled by an Apple Macintosh Model 512K/800 microcomputer (Apple Computer, Cupertino, Calif.) using a Rainin MacRabbit computer program (Rainin Instrument, Woburn, Mass.).

Initial purification of crude peptides was carried out on a Synchropak RP-4 preparative reversed-phase $C_4$ column (250×21.2 mm I.D., 300 Å pore size 5 µm particle size; Dionex Canada, Mississauga, ON).

Peptides were synthesized using the general procedure for solid-phase peptide synthesis as described here. All amino groups with the exception of FMOC-Tyr, were protected at the α-amino position with the BOC-group and the following side-chain protecting groups were used: benzyl ether (Ser), tert-butyl (Tyr), toluenesulfonyl (Arg and His). All amino acids were double coupled as preformed symmetrical anhydrides (with the exception of FMOC-Tyr which was coupled as an HOBT active ester), first in DMF and then dichloromethane. Difficult couplings were monitored using ninhydrin and, in the event that coupling efficiency was less than 99% the amino acid was coupled manually a third time as an active ester, followed by acetylation.

Boc-groups were removed at each cycle with an 80 sec. reaction with 33% TFA/dichloromethane (v/v), followed by a second reaction with 50% TFA/dichloromethane (v/v) for 18.5 min. Neutralization were carried out using 2×1 min washes with 20% DIEA/DMF (v/v). Following couplings, when necessary, any unreacted free amino groups present were acetylated with 25% acetic anhydride/dichloromethane (v/v) for 10 min. The peptides were cleaved from the resin support by treatment with hydrogen fluoride (10 ml/g resin) containing 10% anisole and 2% 1,2-ethanedithiole for 1 hr at –4° C.

Crude peptides were purified initially on the Synchrom preparative column using a linear AB gradient (1% B/min), at a flow-rate of 10 ml/min, where solvent A was 0.5% aqueous TFA and solvent B was 0.05% TFA in acetonitrile.

All analytical runs were performed under the same conditions for the peptide purification except for a flow rate of 0.25 ml/min.

P1: FMOC-Tyr-Ser-Val-OH

P1 was prepared by standard BOC chemistry methods as described above. P1 was purified by RP-HPLC.

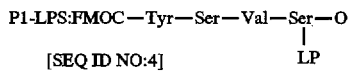

P1-LPS:FMOC—Tyr—Ser—Val—Ser—O  
        |  
[SEQ ID NO:4]   LP

The N-hydroxysuccinimide ester was prepared using DCC in dioxane saturated solution. The sodium salt of LPS was dissolved in pH 7 bicarbonate buffer and added to the ester. The product was then purified by RP-HPLC.

FMOC—Tyr—Ser—Val—Ser—OH  
        |  
[SEQ ID NO:4]   LP

The free acid version of the above structure was prepared by acidifying by addition of sodium citrate to pH 2.8 and extracting using ethylacetate. The structure

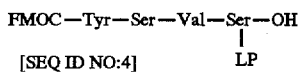

FMOC—Tyr—Ser—Val—Ser—OH  
        |  
[SEQ ID NO:4]   LP was obtained by evaporation using a rotary evaporator P2: $NH_2$-His-Phe-Arg-O$^-$ The structure $NH_2$-His-Phe-Arg-O$^-$ was prepared by standard BOC chemistry methods as described above. The product was purified by RP-HPLC then titrated to pH 7 with sodium bicarbonate.

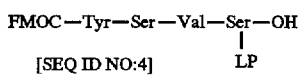

P1-LPS-P2:FMOC—Tyr—Ser—Val—Ser—His—Phe—Arg—O$^-$  
                    |  
[SEQ ID NO:5]   LP

The NHS ester of the product having the structure

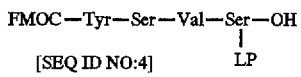

FMOC—Tyr—Ser—Val—Ser—OH  
        |  
[SEQ ID NO:4]   LP was prepared using DCC in a dioxane/THF mixture saturated solution. The product $NH_2$-His-Phe-Arg-O$^-$ was dissolved in pH 7 bicarbonate buffer and added to the ester.

Figure 8:
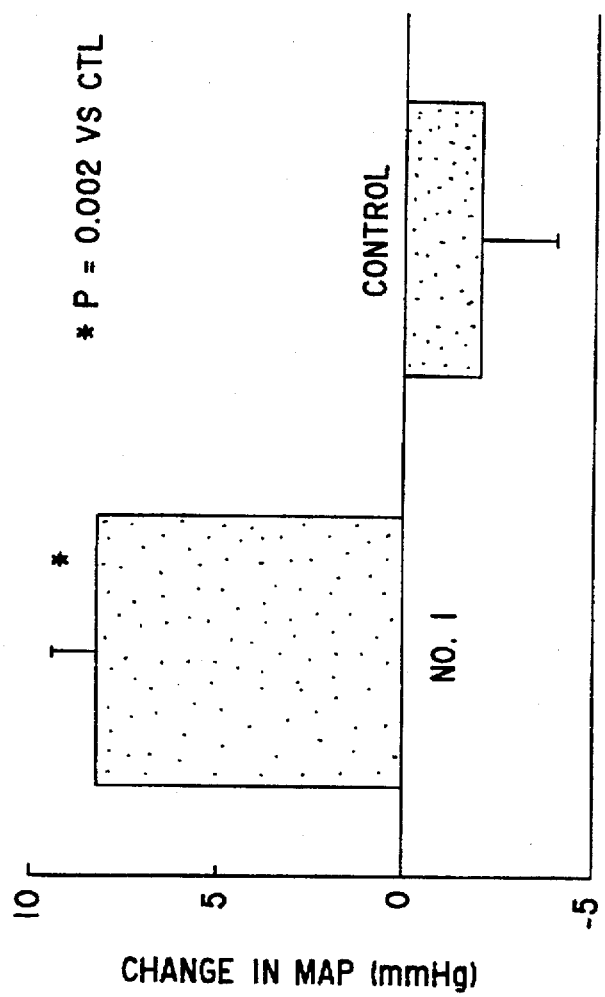
FIG. 8 shows the peak effect of FMOC-synthesis PHF component on blood pressure in normotensive rats. The results are the typical peak sustained increase in blood pressure as seen in the standard bioassay method.
Figure 9:
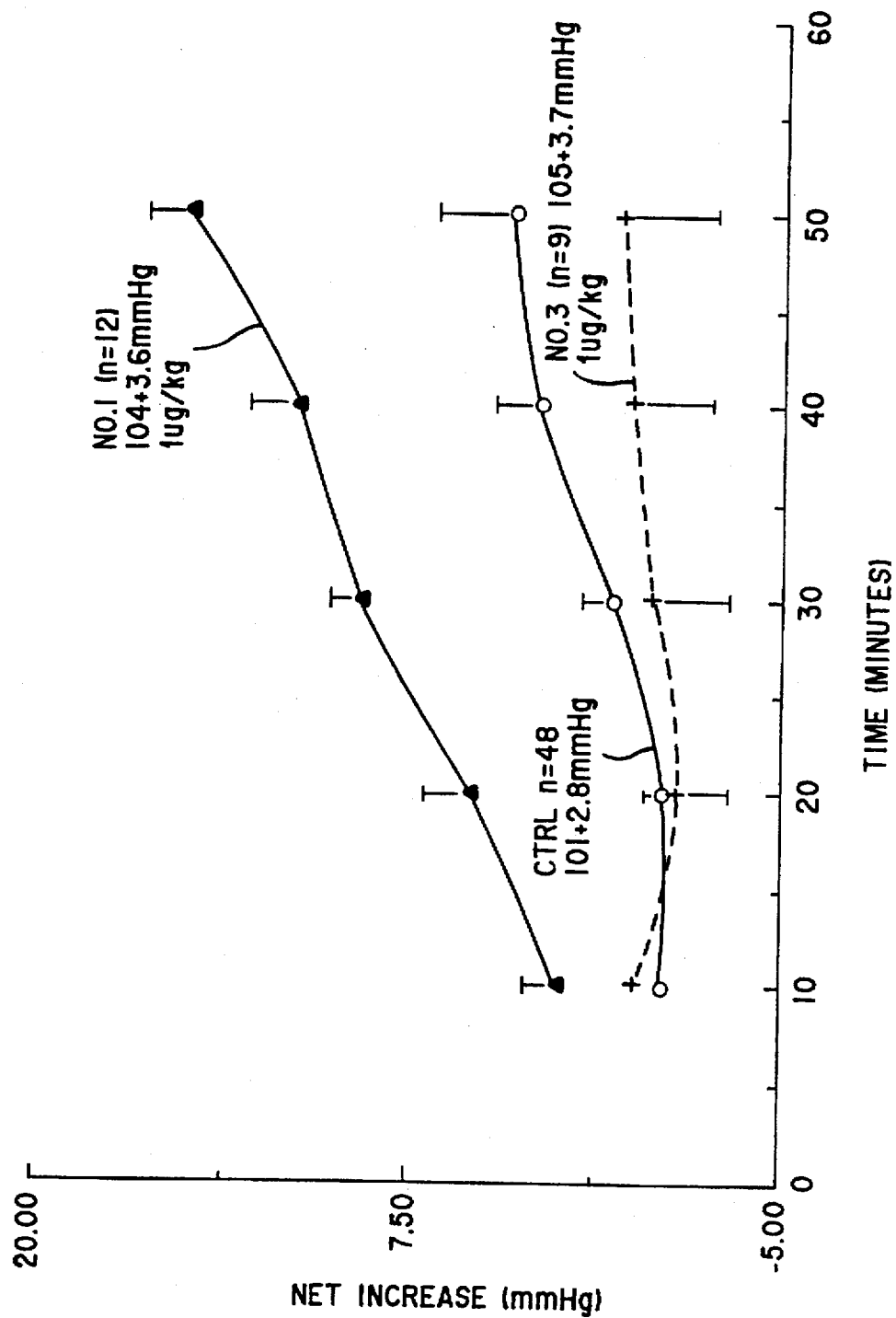
FIG. 9 shows FMOC-synthesis PHF component reveals a typical PHF-like increase in blood pressure that is prevented by digestion with phospholipase D.

The effects of P1-LPS and P1-LPS-P2 were then tested for their in vitro effect on blood pressure in the normotensive rat, as described in Example 1. The results for P1-LPS-P2 (denoted No. 1) are presented in FIG. 8. This compound produced a delayed prolonged hypertensive response. P1-LPS produced minimal hypertensive response. The results for FMOC incubated with phospholipase D (denoted No. 3) are presented in FIG. 9. Phospholipae D digestion of P1-LPS-P2 inactivated the hypertensive response, in a manner similar to the digestion of plasma PHF presented above (FIG. 9).

EXAMPLE 6

$Na^+K^+$ ATPase Activity $Na^+K^+$ ATPase activity was measured as the ouabain-sensitive $^{86}Rb$ uptake in rat tail artery using the method of Deth et al. Briefly, male Sprague-Dawley rats weighing 300 to 400 g were sacrificed by pentobarbital overdose, and the tail arteries removed and cut into strips. The strips were rinsed in ice-cold Krebs solution (composition: NaCl, 117 mM; KCl, 5 mM; $NaHCO_3$, 27 mM, $NaH_2PO_4$, 1 mM, $MgSO_4$, 1.2 mM, $CaCl_2$, 1.25 mM, glucose 11.0 mM) and incubated in oxygenated (95% $O_2$, 5% $CO_2$) Krebs buffer at 37° C. for 2 hours. For the final 30 minutes, Krebs solution with no KCl and 122 mM NaCl was used to sodium-load the tissues. Following this incubation, the strips were transferred to tubes containing Krebs buffer and 1 µCi of $^{86}Rb$, giving a final $RbCl_2$ concentration of 5 mM. Various incubation media consisting of the above-described incubation solution plus 30% SHR plasma (Rb concentration kept constant in all cases) plus 1 mM ouabain and incubation plus 30% plasma plus 1 mM ouabain. Strips were incubated in the respective solutions for 18 minutes, then rinsed in four changes of ice-cold Krebs solution, blotted, weighed and counted in a gamma counter. The effect of the various incubations on $^{86}Rb$ uptake was analyzed by ANOVA using the Student-Neuman-Keuuls test for post-hoc comparisons. All results are expressed as mean±SD.

Figure 10:
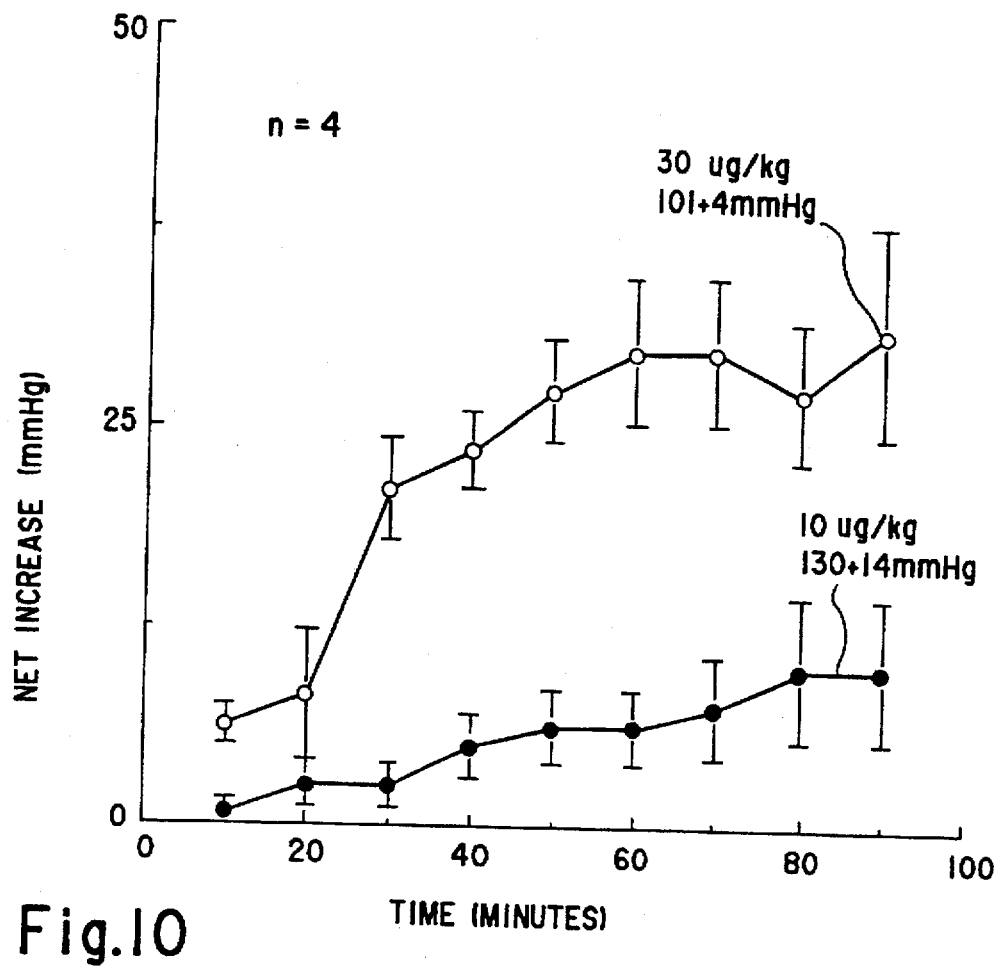
FIG. 10 shows that LPS causes a delayed sustained increase in blood pressure in normotensive rats.
Figure 11:
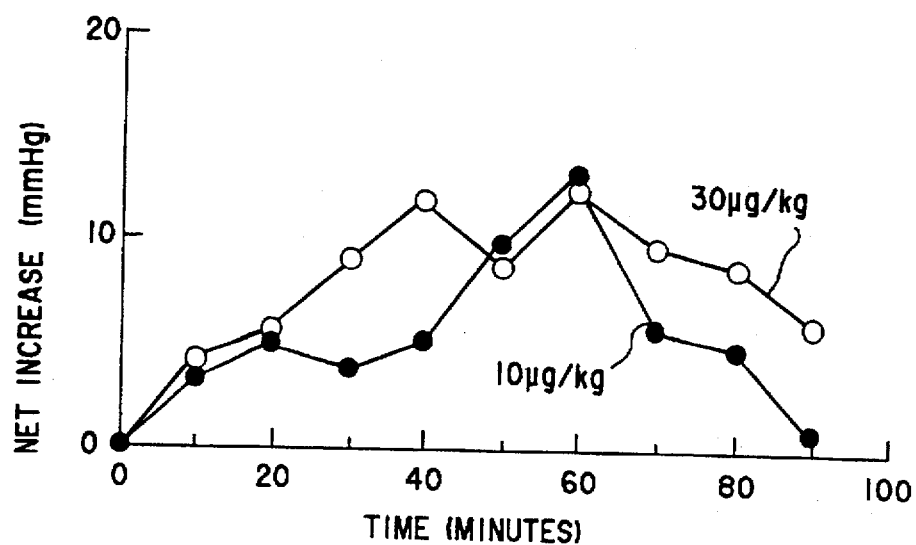
FIG. 11 shows that LPI causes a delayed, sustained increase in blood pressure in normotensive rats.

The results of the effects of lysophospholipids on $^{86}Rb$ uptake into vascular smooth muscle as an indicator of Na/K—ATPase activity are shown below. These lysophospholipids also show a delayed, prolonged hypertensive response similar to PHF (FIGS. 10 and 11).

Lysophosphatidyl serine (30 micromolar) shows a 46% increase in $^{86}Rb$ uptake (p<0.01).

Lysophosphatidyl inositol (600 micromolar) shows a 31% increase in $^{86}Rb$ uptake (p<0.05).

This stimulation in NaKATPase activity is similar for authentic PHF.

EXAMPLE 7

Blood Vessel Tension Measurement

The method was essentially similar to the one described by Pang, et al. (1980). Sprague-Dawley rats of either sex were anesthetized with pentobarbital (50 mg/kg) and the tail artery or aorta were isolated and removed and then placed in KHS buffer (115 mM NaCl, 5 mM KCl, 2.1 mM $CaCl_2$, 1.2 mM $MgSO_4$, 1.2 mM $NaH_2PO_4$, 25 mM $NaHCO_3$, and 11 mM glucose) oxygenated with 95% $O_2$, 5% $CO_2$. The vessels were cut helically and strips of approximately 1.5 cm were secured in a Sawyer-Bartlestone chamber containing KHS. The force development of the helical strips was measured with a Grass FT 0.03 force displacement transducer and recorded on a Grass Model 79D polygraph. Isolated tail artery helical strips were equilibrated for 1 hour prior to addition of any vasoconstricting agents. The strips were preloaded with a resting tension of 0.7 g and incubated at 37° C. (Pang et al., 1985). In all cases, the responsiveness of strips was first tested by adding 60 mM KCl and only responsive tissue was used in experiments. There were two series of experiments.

Two consecutive dose responses to NE in tension development with 1 hour interval were compared. The tissue was washed out after adding first accumulated doses of NE and incubated in normal KHS buffer for 20 mins. The control solvent or testing substances (PHF or LP compounds) were then applied and incubated for another 40 mins. The tissue was challenged again with the second accumulated doses of NE.

The tissue was incubated in $Ca^{2+}$ free KHS buffer for 5 minutes. The tissue was then exposed to the control solvent or testing substances for another 20 mins before the application of accumulated doses of $Ca^{2+}$.

Figure 2:
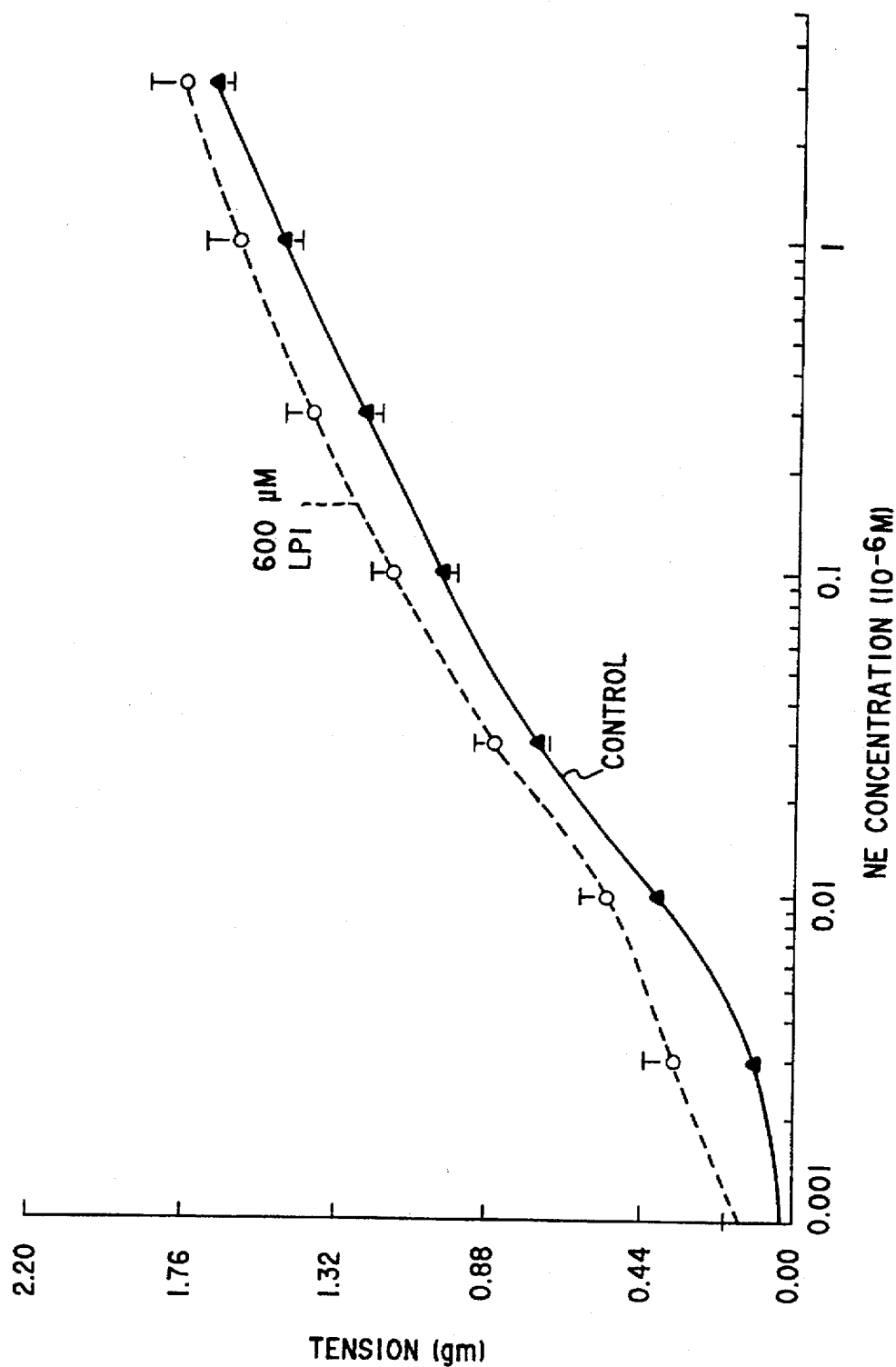
FIG. 2 shows the effect of LPI on tension development induced by NE in rat tail artery. LPI potentiates NE-induced increase tension as does PHF.
Figure 12:
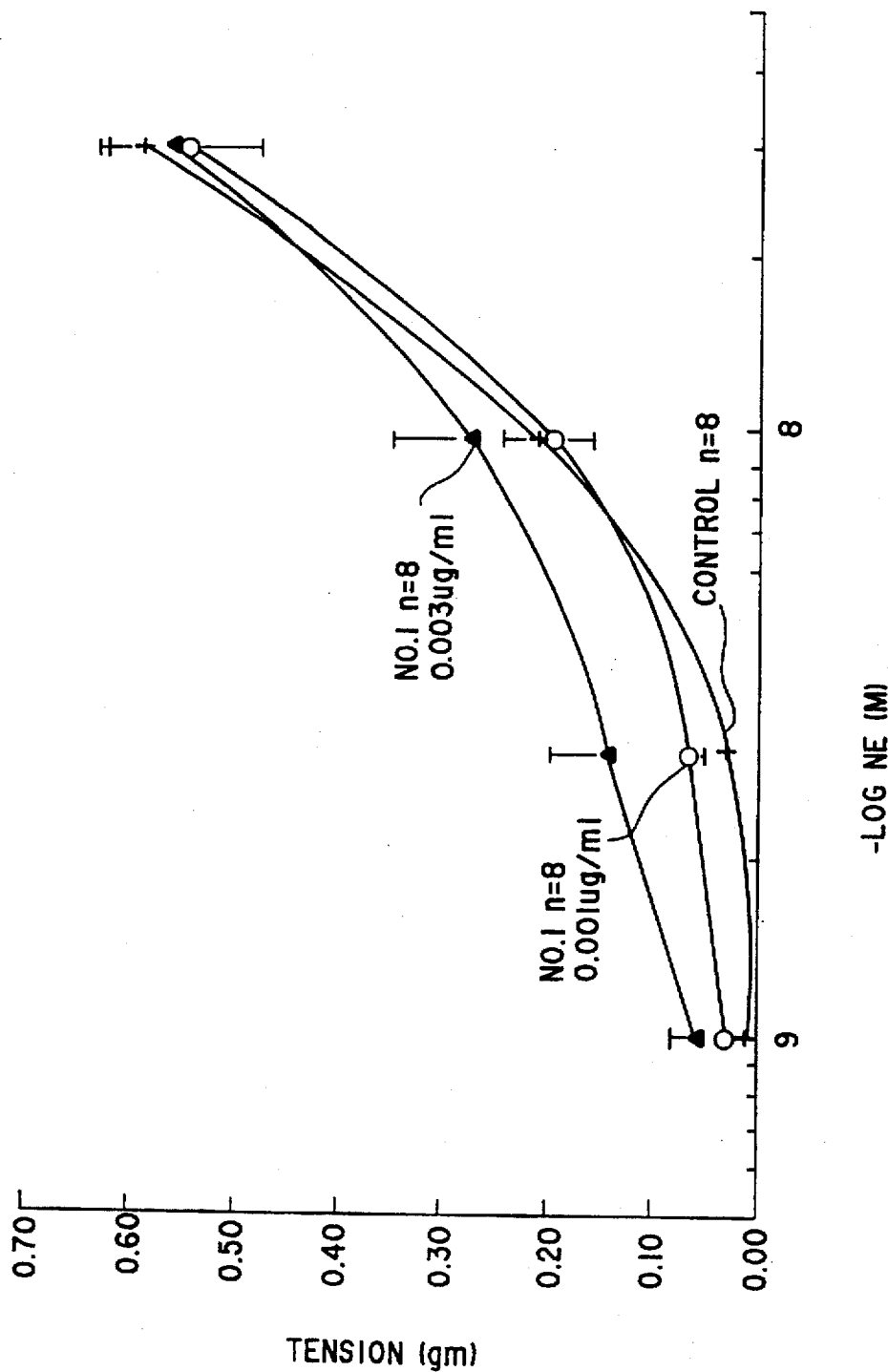
FIG. 12 shows that FMOC-synthesis PHF components potentiates norepinephrine-induced increase in tension in rat tail artery strips.

The results of the tests are shown in FIGS. 1 and 2. In FIG. 1, purified PHF potentiates the norepinephrine (NE) induced tension development by tail artery especially at low doses of norepinephrine. FIG. 2 shows the potentiations of norepinephrine induced tension by lysophosphatidyl inositol. P1-LPS-P2 also potentiates the norepinephrine induced tension (FIG. 12) in a manner similar to PHF and lysophosphatidyl inositol.

EXAMPLE 8

Vascular Smooth Muscle Cell Culture Method

All studies were performed in vascular smooth muscle cells isolated from Sprague Dawley (SD) rat tail artery as described in Wang, et al. (Wang, et al. 1989) with modification. Male SD rats (100–200 g body weight) were anaesthetized with sodium pentobarbital (65 mg/kg body weight intraperitoneally) and the tail artery dissected out and immersed in cold Ca and Mg free Hanks' balanced salt solution (HBSS, Gibco). The blood was washed off from the artery and the connective tissue was then removed. Using a dissecting microscope inside a laminar flow hood, the artery was cut into pieces of about 1.5 cm and placed in 4° C. Ca free HBSS for 30 minutes. After this incubation, the medium was changed to HBSS enzyme solution I (0.2 mM Ca) which was composed of collagenase/dispase (1.5 mg/ml, Boehringer Mannheim GmbH), elastase (0.5 mg/ml, sigma type II-a), trypsin inhibitor (1 mg/ml, Sigma type I-s) and bovine serum albumin (2 mg/ml, fatty acid-free, Sigma). The tissue was incubated in this solution for 60 minutes. The medium was then changed to HBSS enzyme solution II which was composed of collagenase (1 mg/ml, Sigma type II), trypsin inhibitor (0.3 mg/ml, Sigma type I-S) and bovine serum albumin (2 mg/ml, Sigma). Incubation in enzyme solution II also lasted 60 minutes. All incubations in enzyme solutions were carried out in $CO_2$ incubator (5% $CO_2$ and 95% room air at 37° C.). Usually two tail arteries were treated simultaneously in 5 ml of enzyme solution. The arteries were then transferred into 5 ml serum free Dulbecco's modified Eagle's medium (DMEM) and triturated using a fire polished pasteur pipette until the medium turned cloudy. For the patch clamp studies, the cell suspension was placed in 35 mm culture dishes in DMEM. After 4–6 hours, 10% fetal calf serum was added to the medium. For the Fura-2 studies, approximately $1\times10^6$ cells were seeded on a microscope coverslip (25 mm circle), which was placed in a 35 mm culture dish in FCS-free DMEM. After 4–6 hours, 10% FCS was added to the medium. The cells were cultured in a $Co_2$ incubator at 37° C. These cells contracted in response to norepinephrine, indicating that they were functional vascular smooth muscle cells (Wang et al., 1989). More than 95% of cells were viable as shown by tryphan blue exclusion method (Bagby, et al. 1971; Ives, et al., 1978).

EXAMPLE 9

Intracellular Calcium Determination

Primary cultured vascular smooth muscle cells were incubated for 45 minutes in DMEM containing 5 µM fura-2 acetoxymethyl ester (Molecular Probes, INC.) at room temperature. During the incubation, cells were kept in a dark compartment. The cells were gently washed five times with 5K buffer (145 mM NaCl, 5 mM KCl, 1 mM $MgCl_2$, 10 mM glucose, 1 mM $CaCl_2$, 0.5 mM $NaH_2PO_4$, 10 mM Hepes, pH 7.4), and kept in the same buffer. After about 5 min, the coverslip with attached cells was placed in a Sykes-Moore chamber of 1-ml volume on the stage of an inverted microscope, and fluorescence measurements were made with a Fluoroplex III sepctrofluorometer (Tracor Northern). This method is essentially the same as described by Grynkiewicz et al. (Grynkiewicz et al. 1985). R is the ratio of fluorescence in the sample excited at 340 and 380 nM which represents intracellular free calcium concentration. Two series of experiments were carried out.

The monolayer cells in 1 mM $Ca^{2+}$ 5K buffer were challenged by testing substances and the change of R was recorded for a certain period of time.

The experiment was carried out in 1 mM $Ca^{2+}$ 5K buffer. The cells were then washed gently with 5K buffer and kept in same buffer for 5 mins. Testing substances were then applied for 45 mins. and R was recorded again, the cells were stimulated with NE again and the R was recorded. After washing the cells with 5K buffer for 3 times, NE was applied again and the change of R was recorded.

Figure 3A:
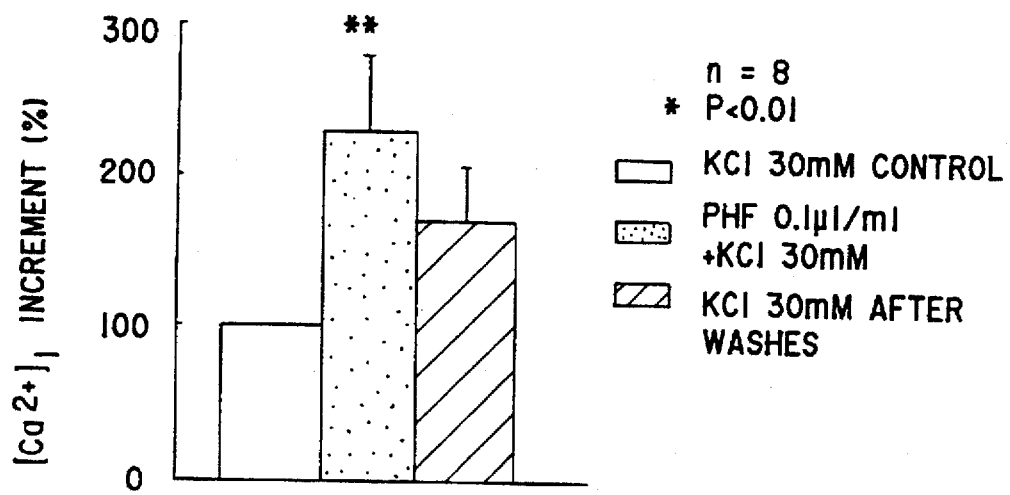
FIG. 3A shows a summary of eight individual experiments. ** Significantly different from control, $p<0.01$.
Figure 3B:
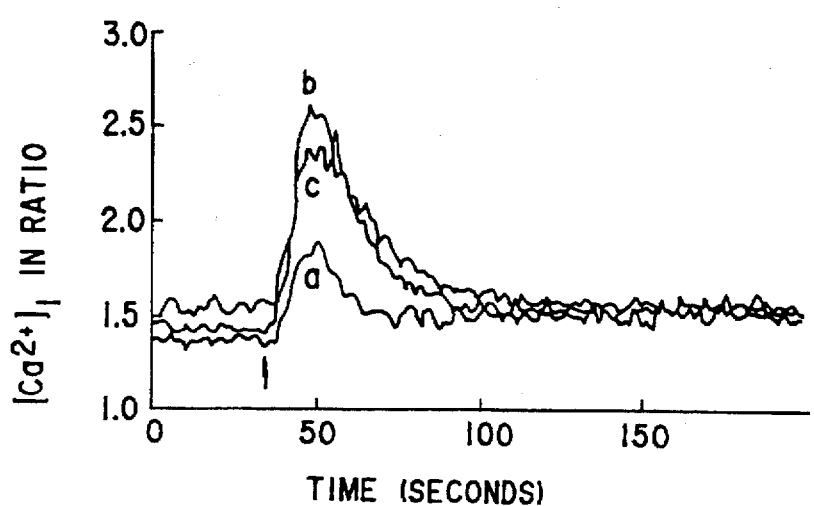
FIG. 3B shows original tracing of one typical experiment. The effect of 30 mM KCl alone (a), in the presence of pure PHF (b), and after washes (c). The cells were incubated with pure PHF for 45 mins. before being challenged with KCl. These three tests were performed sequentially on the same group of cells.
Figure 13A:
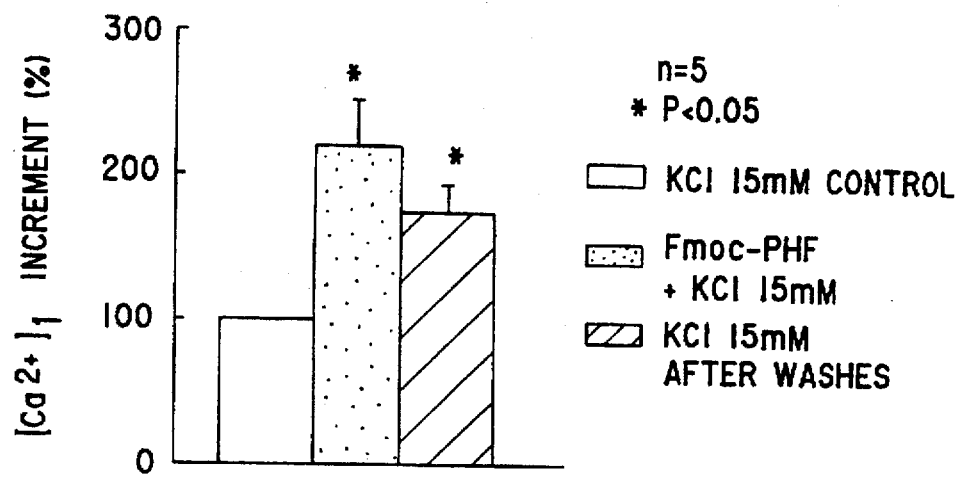
FIG. 13A shows a summary of five individual experiments. The $[Ca^{2+}]_i$ increment in control group is 22.52±4.82 (nM). *Significantly different from the control, $p<0.05$.
Figure 13B:
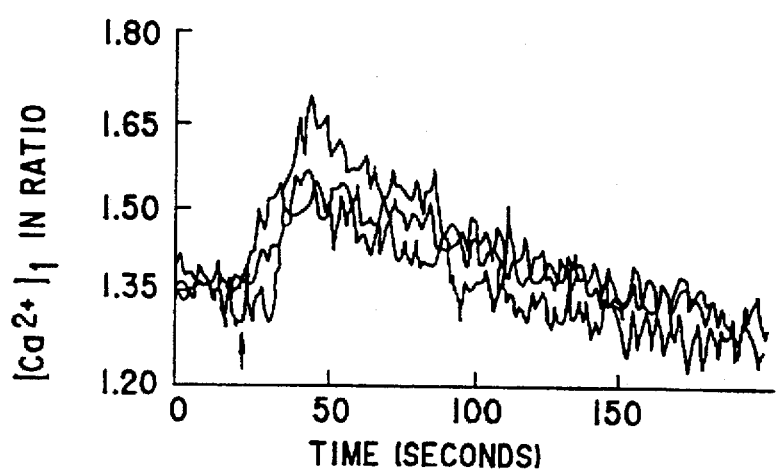
FIG. 13B shows the original tracing of one typical experiment. The effect of 15 mM KCl alone (a), in the presence of FMOC-PHF (b), and after washes (c). The cells were incubated with FMOC-PHF for 45 mins. before challenge with KCL. These three tests were performed sequentially on the same group of cells.
Figures 17A, 17B, 17C, 17D:
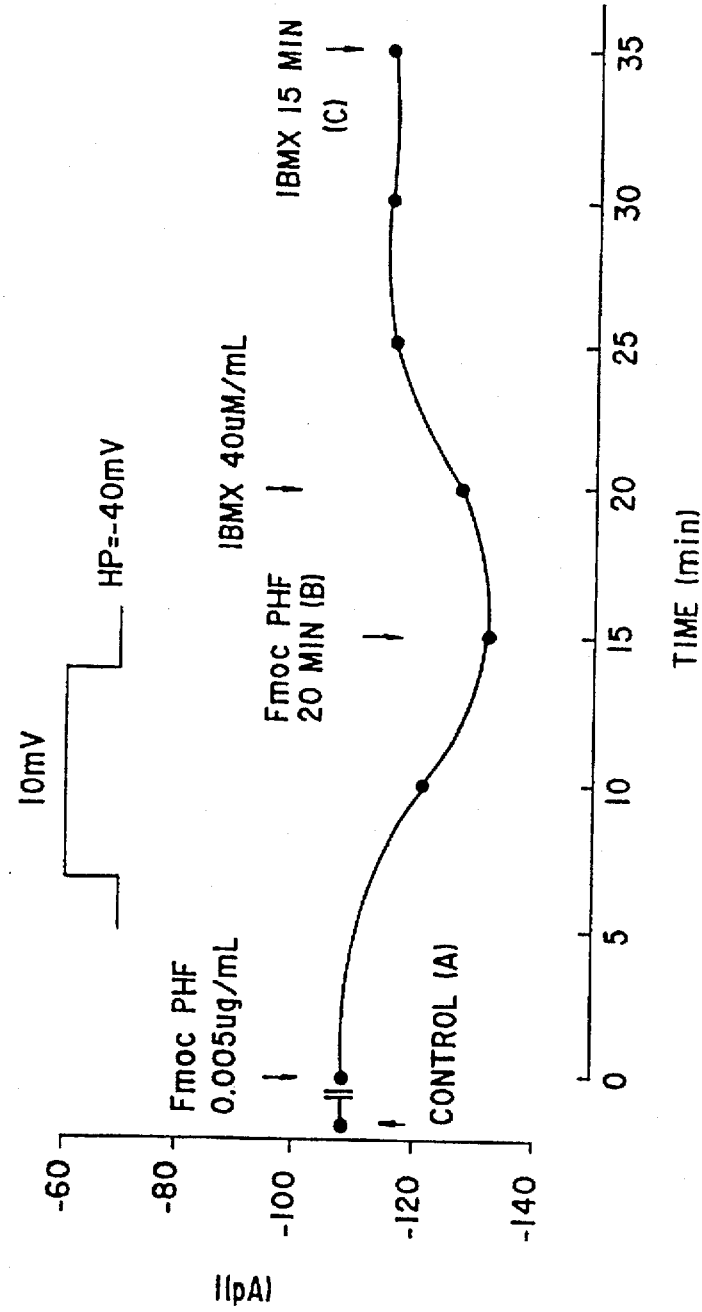
FIG. 17 shows the effect of FMOC-PHF on calcium channel currents and reversal by IBMX.

Results of the tests are shown in FIGS. 3 and 4. FIG. 3 shows the increase in intracellular calcium induced by PHF and FIG. 4 shows an increase induced by lysophosphatidyl choline. FIG. 13 shows the effect of FMOC-PHF on intracellular calcium increase induced by KCl, and that FMOC-PHF potentiated in the effect of KCl.

EXAMPLE 10

Activation of CaM (calmodulin)-Dependent PDE

The measurement of cGMP-PDE activity is based on the conversion of [$^3$H]cGMP into [$^3$H]GMP and its subsequent hydrolysis by snake venom into [$^3$H]Guanosine (Wallace, et al., 1983; Wells, et al., 1975). The testing substance was added to a mixture containing 60 mM TES, 3 mM $MgCl_2$, 0.8 mg/ml BSA, 25 µM EGTA, 50 uM $CaCl_2$, 1 mM DTT, 0.5 µM cGMP and [$^3$H]–cGMP (10–15×10$^3$cpm) at a final pH of 7.5 for a total volume of 200 µl. The reaction was started by the addition of a fixed quantity of CaM-deficient PDE (Sigma Chemical Co., St. Louis, Mo.). Incubation carried out for 15 mins at 30° C., was terminated by boiling for 5 mins. The second reaction was initiated by the addition of 20 μl (10 mg/ml) of snake venom (Crotalus atrox). After 10 mins., the incubation was stopped with 700 μl of a second termination medium containing 0.1 mM guanosine. The total incubation mixture was then applied onto a column of QAE-Sephadex A-25 (formate form) to separate labeled nucleotides from the labeled nucleosides formed. The resin was eluted with 4 ml of 20 mM ammonium formate (pH 6.5), and the radioactivity of the eluate containing [$^3$H] guanosine was determined in a liquid scintillation counter. A standard curve of PDE stimulation by CaM was obtained by the addition of different concentrations of purified bovine heart CaM (Sigma) (0.1–200 ng/tube). The testing substance was also assayed in the presence of 10 ng/tube CaM. The maximum stimulation of PDE was obtained in the presence of 100 ng/tube CaM.

Figure 5:
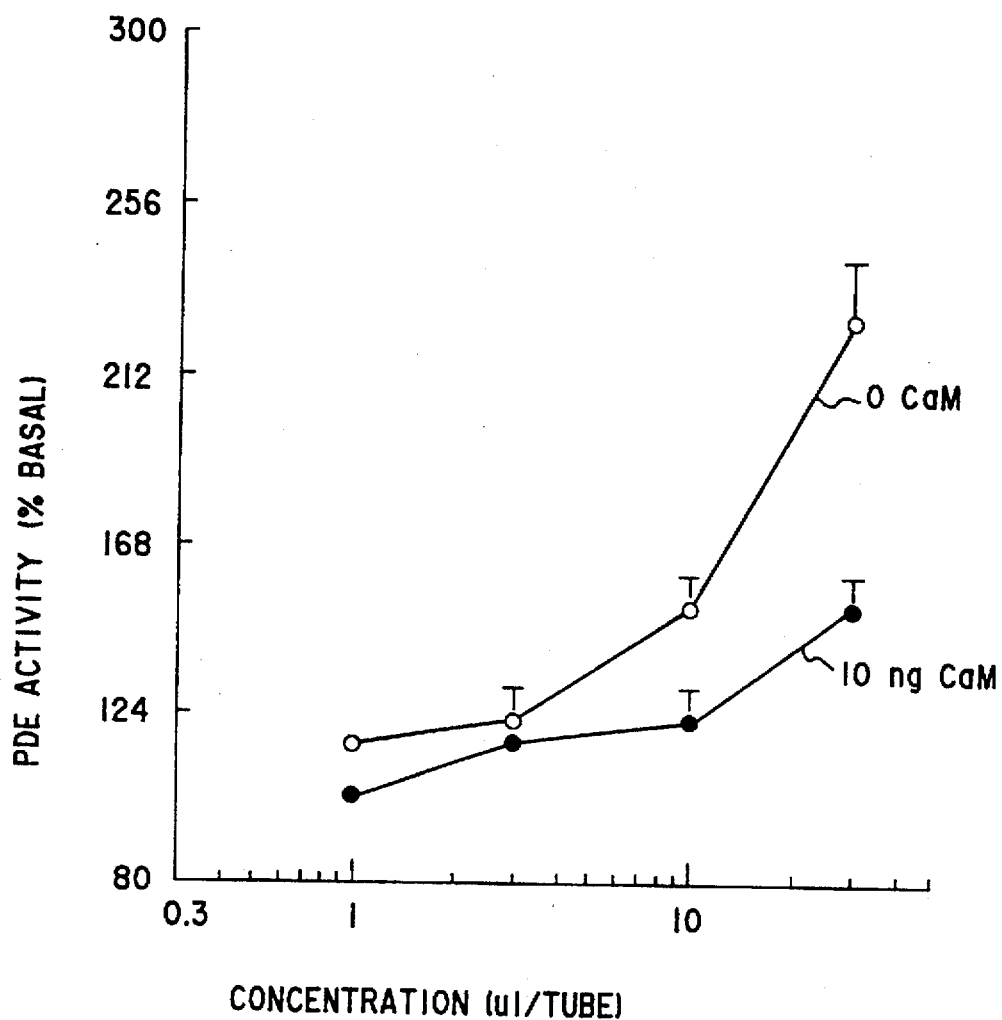
FIG. 5 shows SHR parathyroid gland culture media will stimulate phosphodiesterase activity.
Figure 6:
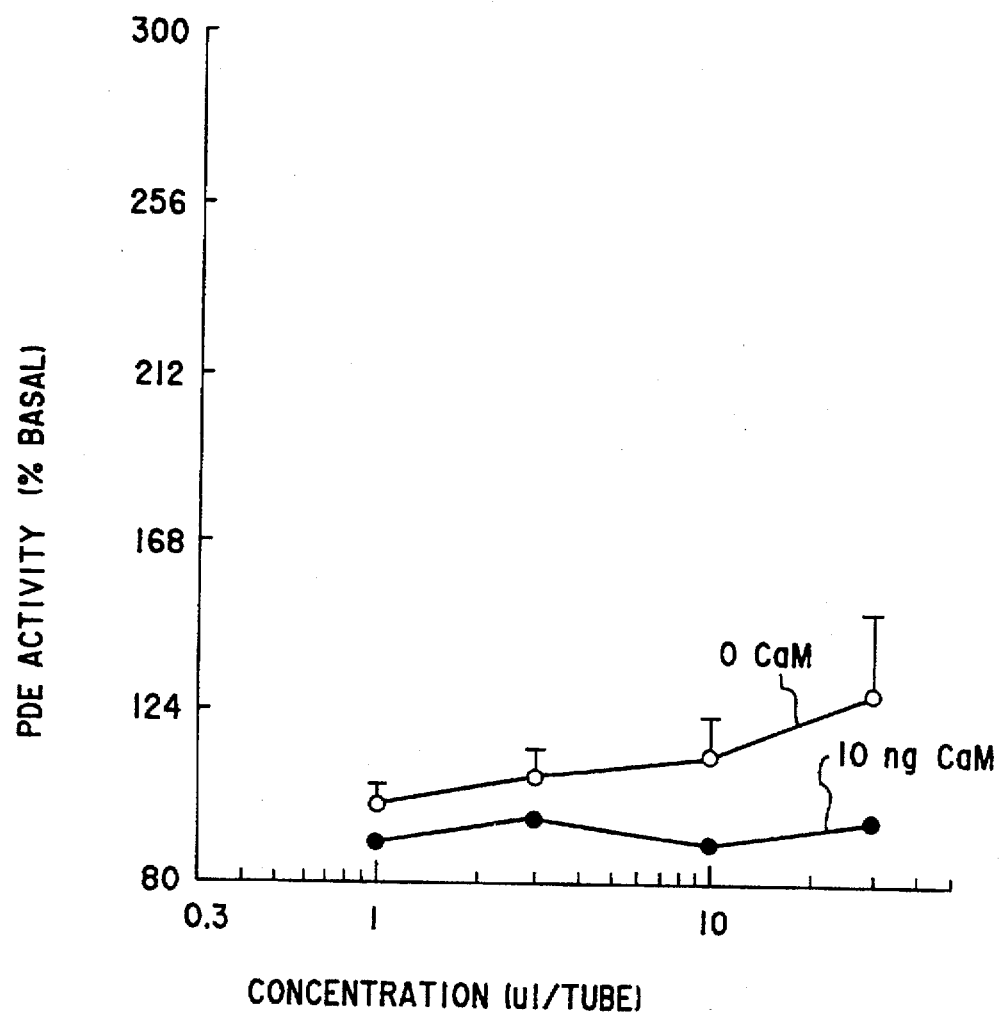
FIG. 6 shows WKY parathyroid gland culture media does not stimulate phosphodiesterase activity.
Figure 7:
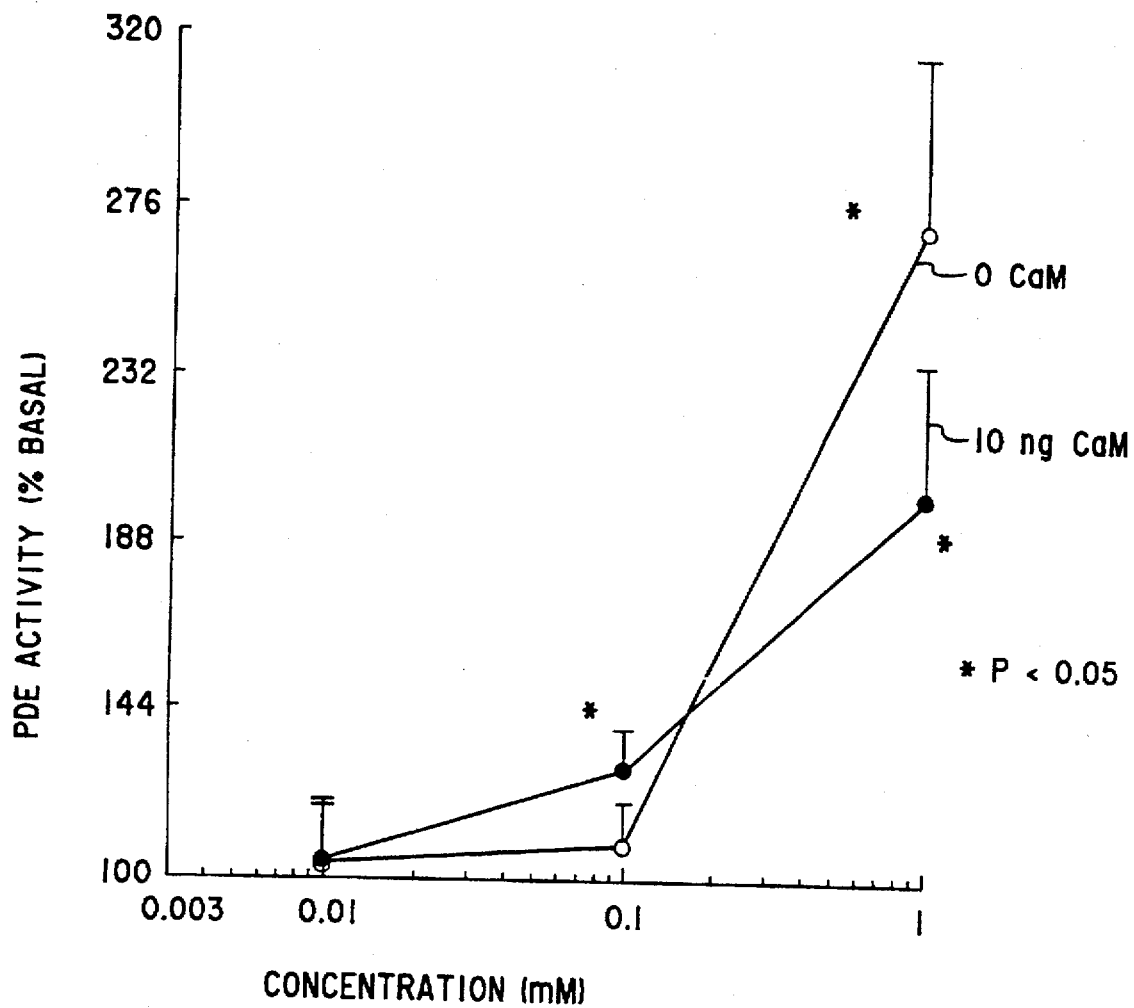
FIG. 7 shows LPS stimulates phosphodiesterase activity.

Results are demonstrated in FIGS. 5, 6 and 7. In FIG. 5, SHR parathyroid gland culture medium increased phosphodiesterase (PDE) activity. WKY parathyroid gland culture mediums, which do not contain PHF, produces no significant increase in PDE activity (FIG. 6). Lysophosphatidyl Serine (FIG. 7) also stimulated PDE activity.

EXAMPLE 11

Enzymatic Production and Activity of PHF Antagonist

The same peptides as in Example 4 are used in this example. Each of the peptides (0.5 mg) and a lipid mixture of Table 2 were incubated with phospholipase D (1 mg) in 50 mM Tris buffer, pH 7.8 in a final volume of 1 ml. Simultaneously, the appropriate controls were also incubated. Incubation was at 37° C. for 1 hour. The reaction was terminated at by heating the samples to 95° C. for 5 minutes. The samples were bioassayed for their ability to antagonize the elevation in blood pressure of normotensive (SD) rats induced by dialyzed, filtered and lyophilized (DF) SHR plasma. Approximately 150 microliters of reaction mixture was injected into each assay rat immediately prior to injection of 1.5 ml of DF SHRplasma. Blood pressure response was monitored for 90 minutes and the results are shown in Table 2. In the biological assay for antagonist activity (Table 2), the ability to block the effects of authentic plasma PHF was determined in the blood pressure assay. The results indicated that substitution of the number 4 serine resulted in antagonistic activity. This substitution may force the attachment of the LP onto the number 2 serine.

EXAMPLE 12

Ca$^{2+}$ Channel Study

Ca$^{2+}$ channel activity was determined in single VSMC isolated form rat tail artery by using the whole cell version of the patch clamp technique (Hamill et al., 1981). Whole cell Ca$^{2+}$ current measurements were carried out by using an Axopatch-1B patch clamp amplifier (Axon Instruments). Patch micropipettes were pulled from borosilicate thin wall glass capillary tubes (OD 1.2 mm, ID 0.9 mm, FHS, Brunswick, Maine, USA) with a two stage micropipette puller (Narishige, PP83, Japan). The micropipettes were fire polished using a microforge (Leitz, Wetzlar, Germany). The tip diameter was approximately 1 μm with a resistance of 2–8 Mega Ohms. The cell attached to the bottom of a 3 cm Petri dish and was bathed in the medium containing 110 mM Tris, 5 mM CsCl, 20 mM HEPES, 30 mM glucose, 20 mM BaCl$_2$, and 0.5 μM TTX. The polished pipette filled with a solution containing 75 mM Cs$_2$-aspartate, 10 mM EGTA, 2 mM ATP, 5 mM MgCl$_2$, 5 mM K-pyruvate, 5 mM K-succinate, 25 mM glucose, 15 mM HEPES, 5 mM creatine phosphate-Na$_2$, and 50 units/ml creatine kinase was placed against the cell membrane using a Narishige hydraulic micromanipulator. Gentle suction was applied via a tubing attached to the pipette holder. By further application of suction, a gigaseal was formed and the patch membrane was broken. The holding potential was set at –40 mV. The barium current (20 mM Ba$^{2+}$ was used as the charge carrier) through the Ca$^{2+}$ channels was elicited by 200 msec depolarization at intervals of 5 sec. The currents were monitored using a digital oscilloscope (Nicolet Instrument Co., Madison, Wis., U.S.A.) and filtered at 3 KHz with a low pass filter (Axon Instruments, Foster City, Calif., U.S.A.). PClamp software (version 5.5) and a labmaster interface (Axon Instruments, Foster City, Calif., U.S.A.) were used to generate the test pulses and to score and analyze the data. The current-voltage plot was constructed using the peak current values (leakage corrected).

FIGS. 14–17 show the results of this study.

TABLE 1

| BIOASSAY FOR PHF-LIKE ACTIVITY-AGONIST | | | | |
|---|---|---|---|---|
| Rxn No. | PEPTIDE | LIPID | PLD | BP |
| 1 | CS2129 | 18:1 | + | (12.0, 14.0, 3.7 6.4, 2.5, 10.6) |
| 2 | CS2129 | 14:0 | + | (1.0, 7.3) |
| 3 | CS2129 | 18:0 | + | 0.6 |
| 4 | CS2129 | 16:0 | + | 16.2 |
| 5 | CS2129 | 2X18:1 | + | 8.3 ± 3.9 |
| 6 | CS2129 | 2X14:0 | + | |
| 7 | CS2129 | 2X18:0 | + | |
| 8 | CS2129 | 2X16:0 | + | |
| 9 | CS2129 | 2X12:0 | + | |
| (control for 5–9) | | | | |
| 10 | — | — | — | –5.8 ± 3.8 |
| 11 | — | 18:1 | — | (0, 7.7) |
| 12 | — | 14:0 | — | –5.8 |
| 13 | — | 18:0 | — | –2.8 |
| 14 | — | 16:0 | — | –6.2 |
| 15 | — | 2X18:1 | — | –1.3 ± 3.7 |
| 16 | — | 2X14:0 | — | |
| 17 | — | 2X18:0 | — | |
| 18 | — | 2X16:0 | — | |
| 19 | — | 2X12:0 | — | |
| 20 | CS2130 | 18:1 | + | –5.4 ± 2.4 |
| 21 | CS2131 | 18:1 | + | 1.6 ± 2.8 |
| 22 | CS2132 | 18:1 | + | (1.6, –2.0 ± 0.9) |
| 23 | NSP | 18:1 | + | 0.3 ± 3.9 |
| 24 | CS2130 | — | — | –7.0 ± 7.0 |
| 25 | CS2131 | — | — | 5.4 ± 4.3 |
| 26 | CS2132 | — | — | (5.7, 6.0 ± 3.2) |
| 27 | NSP | — | — | 0.5 ± 2.5 |

2X 12:0 = lauric acid, phosphatidic acid
14:0 = myristic acid, lysophosphatidic acid
2X14:0 = myristic acid, phosphatidic acid
16:0 = palmitic acid, lysophosphatidic acid
2X16:0 = palmitic acid, phosphatidic acid
18:0 = stearic acid, lysophosphatidic acid
2X18:0 = stearic acid, phosphatidic acid
18:1 = oleic acid, lysophosphatidic acid
2X18:1 = oleic acid, phosphatidic acid

TABLE 2

BIOASSAY FOR PHF BLOCKING ACTIVITY-ANTAGONIST

| Rxn No. | PEPTIDE | LIPID | PLD | BP |
|---|---|---|---|---|
| 1 | CS2129 | 18:1 | + | not tested |
| 2 | CS2129 | 14:0 | + | (1.0, 4.5) |
| 3 | CS2129 | 18:0 | + | 8.4 |
| 4 | CS2129 | 16:0 | + | −5.7 |
| 5 | CS2129 | 2X18:1 | + | 6.0 |
| 6 | CS2129 | 2X14:0 | + | 5.7 |
| 7 | CS2129 | 2X18:0 | + | not interpretable |
| 8 | CS2129 | 2X16:0 | + | |
| 9 | CS2129 | 2X12:0 | + | |
| (control for 5–9) | | | | |
| 10 | — | — | — | |
| 11 | — | 18:1 | — | |
| 12 | — | 14:0 | — | 10.0 |
| 13 | — | 18:0 | — | 4.5 |
| 14 | — | 16:0 | — | −1.0 |
| 15 | — | 2X18:1 | — | |
| 16 | — | 2X14:0 | — | |
| 17 | — | 2X18:0 | — | |
| 18 | — | 2X16:0 | — | |
| 19 | — | 2X12:0 | — | |
| 20 | CS2130 | 18:1 | + | 3.2 |
| 21 | CS2131 | 18:1 | + | 0.4 * |
| 22 | CS2132 | 18:1 | + | −1.75* |
| 23 | NSP | 18:1 | + | −3.0 variable |
| 24 | CS2130 | — | — | 5.8 |
| 25 | CS2131 | — | — | 3.7 |
| 26 | CS2132 | — | — | 6.2 |
| 27 | NSP | — | — | 5.4 |

\* = good antagonistic activity
2X12:0 = lauric acid, phosphatidic acid
14:0 = myristic acid, lysophosphatidic acid
2X14:0 = myristic acid, phosphatidic acid
16:0 = palmitic acid, lysophosphatidic acid
2X16:0 = palmitic acid, phosphatidic acid
18:0 = stearic acid, lysophosphatidic acid
2X18:0 = stearic acid, phosphatidic acid
18:1 = oleic acid, lysophosphatidic acid
2X18:1 = oleic acid, phosphatidic acid

What is claimed is:

1. A purified and isolated parathyroid hypertensive factor component comprising a polypeptide linked to a phospholipid wherein said parathyroid hypertensive factor component produces a delayed increase in blood pressure of a normotensive rat when administered thereto, said increase in blood pressure occurring at the same time as an increase in extracellular calcium uptake by vascular smooth muscle and having a molecular weight different from naturally occurring parathyroid hypertensive factor.

2. The parathyroid hypertensive factor component according to claim 1, wherein the polypeptide has from 5–20 amino acid residues.

3. The parathyroid hypertensive factor component according to claim 2, wherein the polypeptide has the structure:

Tyr-Ser-Val-Ser-His-Phe-Arg    (SEQ ID NO:1)

4. The parathyroid hypertensive factor component according to claim 3, wherein the phospholipid is lysophosphatidic acid.

5. The parathyroid hypertensive factor component according to claim 3, wherein the phospholipid is phosphatidic acid.

6. The parathyroid hypertensive factor component according to claim 3, wherein the phospholipid is linked to the polypeptide at one of the serine residues.

7. The parathyroid hypertensive factor component according to claim 6, wherein the phospholipid is linked to the polypeptide at the serine residue in position 4.

8. The parathyroid hypertensive factor component according to claim 1 which has a molecular weight between about 1,000 and about 2,700 daltons.

9. The parathyroid hypertensive factor component according to claim 1, further comprising a biologically active compound.

10. The parathyroid hypertensive factor component according to claim 1, further comprising a detectable marker.

11. A purified and isolated parathyroid hypertensive factor component having the property of delayed onset of an increase in blood pressure of a normotensive rat when administered thereto, said increase in blood pressure temporally correlating with an increase in extracellular calcium uptake by vascular smooth muscle, in a manner similar to naturally occurring PHF which has been purified from a hypertensive individual, which is structurally different from parathyroid hypertensive factor and which has the following structure:

$$\begin{array}{c} H_2C-O-R_1 \\ | \\ HC-OR_2 \\ | \\ CH_2 \\ | \\ Y \\ | \\ HO-P=O \\ | \\ X \\ | \\ A-[Tyr-Ser-Val-Ser-His-Phe-Arg]_n-B \end{array}$$

[SEQ ID NO:1]

wherein $R_1$ is hydrogen, a $C_1$–$C_{22}$ alkyl, a $C_1$–$C_{22}$ alkenyl or at least one fatty acid group, $R_2$ is as previously defined for $R_1$; each of X and Y are oxygen or sulfur; each of A and B are from 0 to 20 additional amino acids with the proviso that at least one of A and B does not have an amino acid sequence corresponding to that of PHF isolated from a hypertensive individual; and n=1 to 5.

12. The parathyroid hypertensive factor component according to claim 11, wherein X is oxygen.

13. The parathyroid hypertensive factor component according to claim 11, wherein Y is oxygen.

14. The parathyroid hypertensive factor component according to claim 11, wherein X and Y are each oxygen.

15. The parathyroid hypertensive factor component according to claim 11, wherein $R_1$ is at least one fatty acid group.

16. The parathyroid hypertensive factor component according to claim 15, wherein said at least one fatty acid is selected from the group consisting of lauric acid, myristic acid, palmitic acid, stearic acid, arachidic acid, behenic acid, lignoceric acid, palmitoleic acid, oleic acid, linoleic acid, α-linolenic acid, γ-linolenic acid, arachidonic acid, EPA and Nervonic acid.

17. The parathyroid hypertensive factor component according to claim 11, wherein $R_2$ is at least one fatty acid group.

18. The parathyroid hypertensive factor component according to claim 17, wherein said at least one fatty acid is selected from the group consisting of lauric acid, myristic acid, palmitic acid, stearic acid, arachidic acid, behenic acid, lignoceric acid, palmitoleic acid, oleic acid, linoleic acid, α-linolenic acid, γ-linolenic acid, arachidonic acid, EPA and Nervonic acid.

19. The parathyroid hypertensive factor component according to claim 11 which has the structure:

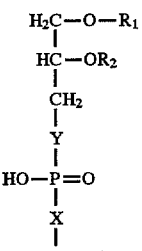

[SEQ ID NO:1]

20. A process for producing a parathyroid hypertensive factor component wherein said component produces a delayed increase in blood pressure of a normotensive rat when administered thereto, said increase in blood pressure occurring at the same time as an increase in extracellular calcium uptake by vascular smooth muscle, in a manner similar to naturally occurring PHF which has been purified from a hypertensive subject, which has a structure different from parathyroid hypertensive factor and which has the following structure:

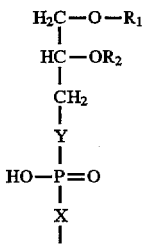

[SEQ ID NO:1]

wherein $R_1$ is hydrogen, a $C_1$–$C_{22}$ alkyl, a $C_1$–$C_{22}$ alkenyl, or at least one fatty acid group; $R_2$ is hydrogen, a $C_1$–$C_{22}$ alkyl, a $C_1$–$C_{22}$ alkyl, or at least one fatty acid group; each of X and Y are oxygen or sulfur; each of A and B are from 0 to 20 additional amino acids with the proviso that at least one of A and B does not have an amino acid sequence corresponding to that of PHF which has been isolated from a hypertensive individual; and n=1 to 5, comprising the steps of:

(a) incubating a mixture comprising a polypeptide having the structure

A-(Tyr-Ser-Val-Ser-His-Phe-Arg)$_n$-B,     (SEQ ID NO:1)

wherein A, B and n are as previously defined and a phospholipid with phospholipase D; and (b) recovering the parathyroid hypertensive factor component formed in step (a).

21. The process for producing the parathyroid hypertensive factor component according to claim 20, wherein said polypeptide is produced by chemical synthesis.

22. The process for producing the parathyroid hypertensive factor component according to claim 20, wherein said phospholipid is lysophosphatidic acid.

23. The process for producing the parathyroid hypertensive factor component according to claim 20, wherein said phospholipid is phosphatidic acid.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
      ( A ) LENGTH: 9 amino acids
      ( B ) TYPE: amino acid
      ( C ) STRANDEDNESS:
      ( D ) TOPOLOGY: linear ( i i ) MOLECULE TYPE: peptide ( i x ) FEATURE:
      ( A ) NAME/KEY: Modified-site
      ( B ) LOCATION: 1 AND 9
      ( D ) OTHER INFORMATION: /note= "Xaa at positions 1 and 9
          are from 0 to 20 additional amino acids."

( i x ) FEATURE:
      ( A ) NAME/KEY: Modified-site
      ( B ) LOCATION: 5
      ( D ) OTHER INFORMATION: /note= "Ser at position 5 may be
          unlinked or linked with a phosphoglyceride."

( x i ) SEQUENCE DESCRIPTION: SEQ ID NO:1:

Xaa  Tyr  Ser  Val  Ser  His  Phe  Arg  Xaa
    1                        5

( 2 ) INFORMATION FOR SEQ ID NO:2:

(i) SEQUENCE CHARACTERISTICS:
    (A) LENGTH: 5 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note= "Xaa at position 1 is from
        0 to 20 additional amino acids."

(ix) FEATURE:
    (A) NAME/KEY: Modified-site
    (B) LOCATION: 5
    (D) OTHER INFORMATION: /note= "Ser at position 5 is
        linked to L- alpha-lysophosphatidyl and O or OH."

(xi) SEQUENCE DESCRIPTION: SEQ ID NO:2:

Xaa  Tyr  Ser  Val  Ser
1                     5

(2) INFORMATION FOR SEQ ID NO:3:

(i) SEQUENCE CHARACTERISTICS:
    (A) LENGTH: 7 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Modified-site
    (B) LOCATION: 2
    (D) OTHER INFORMATION: /note= "Ser at position 2 is
        linked to a phospholipid."

(ix) FEATURE:
    (A) NAME/KEY: Modified-site
    (B) LOCATION: 4
    (D) OTHER INFORMATION: /note= "Xaa at position 4 is any
        amino acid other than Ser."

(xi) SEQUENCE DESCRIPTION: SEQ ID NO:3:

Tyr  Ser  Val  Xaa  His  Phe  Arg
1                     5

(2) INFORMATION FOR SEQ ID NO:4:

(i) SEQUENCE CHARACTERISTICS:
    (A) LENGTH: 4 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note= "Tyr at position 1 is
        linked to PI-LPS:FMOC or FMOC."

(ix) FEATURE:
    (A) NAME/KEY: Modified-site
    (B) LOCATION: 4
    (D) OTHER INFORMATION: /note= "Ser at position 4 is
        linked to a phospholipid and O or OH."

(xi) SEQUENCE DESCRIPTION: SEQ ID NO:4:

Tyr  Ser  Val  Ser

1

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Tyr at position 1 is
            linked to P1-LPS-P2:FMOC-."

( i x ) FEATURE:
        ( A ) NAME/KEY: Modified-site
        ( B ) LOCATION: 7
        ( D ) OTHER INFORMATION: /note= "Arg at position 7 is
            linked to O."

( x i ) SEQUENCE DESCRIPTION: SEQ ID NO:5:

Tyr  Ser  Val  Ser  His  Phe  Arg
    1                        5

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:6:

Tyr  Ser  Val  Lys  His  Phe  Arg
    1                        5

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:7:

Tyr  Ser  Val  Tyr  His  Phe  Arg
    1                        5

( 2 ) INFORMATION FOR SEQ ID NO:8:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:8:

Tyr  Ser  Val  Leu  His  Phe  Arg
    1                        5

( 2 ) INFORMATION FOR SEQ ID NO:9:

(i) SEQUENCE CHARACTERISTICS:
    (A) LENGTH: 8 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:9:

Gly Leu Asn Arg Lys Tyr Leu Val
1               5